US007866220B2

(12) United States Patent
Oki et al.

(10) Patent No.: US 7,866,220 B2
(45) Date of Patent: Jan. 11, 2011

(54) METHOD FOR COLLECTING GASEOUS SAMPLE

(75) Inventors: Akio Oki, Kyoto (JP); Hiroaki Oka, Osaka (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 12/618,342

(22) Filed: Nov. 13, 2009

(65) Prior Publication Data

US 2010/0116068 A1 May 13, 2010

Related U.S. Application Data

(63) Continuation of application No. PCT/JP2009/052255, filed on Feb. 4, 2009.

(30) Foreign Application Priority Data

Feb. 5, 2008 (JP) ............................ 2008-024667

(51) Int. Cl.
*G01N 1/22* (2006.01)

(52) U.S. Cl. .................... 73/863.21; 73/23.2; 73/31.05; 239/704

(58) Field of Classification Search .............. 73/863.21, 73/23.2, 23.3, 31.01, 31.02, 31.03, 31.05; 600/532; 239/3, 704
See application file for complete search history.

(56) References Cited

U.S. PATENT DOCUMENTS 4,885,076 A 12/1989 Smith et al.
5,098,657 A 3/1992 Blackford et al.
2009/0275852 A1 * 11/2009 Oki et al. .................... 600/532

FOREIGN PATENT DOCUMENTS

| | | |
|---|---|---|
| JP | 07-190990 | 7/1995 |
| JP | 07-270285 | 10/1995 |
| JP | 10-206387 | 8/1998 |
| JP | 2001-318069 | 11/2001 |
| JP | 2002-511792 | 4/2002 |
| JP | 2004-210154 | 7/2004 |
| JP | 2006-068711 | 3/2006 |
| JP | 3952052 | 5/2007 |
| WO | WO 98/58745 | 12/1998 |

* cited by examiner

*Primary Examiner*—Daniel S Larkin
(74) *Attorney, Agent, or Firm*—McDermott Will & Emery LLP

(57) ABSTRACT

The present invention of collecting a gaseous sample employs a sealable container, an inlet mounted at a part of the container, an outlet mounted at another part of the container, an atomizing electrode mounted in the container, a primary refrigerator mounted adjacent to the atomizing electrode, an opposite electrode mounted in the container, an acicular capture electrode mounted adjacent to the opposite electrode, and a secondary refrigerator mounted adjacent to the capture electrode. Charged microparticles are prepared by chilling the gaseous sample and producing condensate of the same. Such charged microparticles are collected by the capture electrode with static electricity, and they are condensed by chilling them. This method prevents the capture electrode from spreading solution thereon.

15 Claims, 14 Drawing Sheets

[Fig. 1]
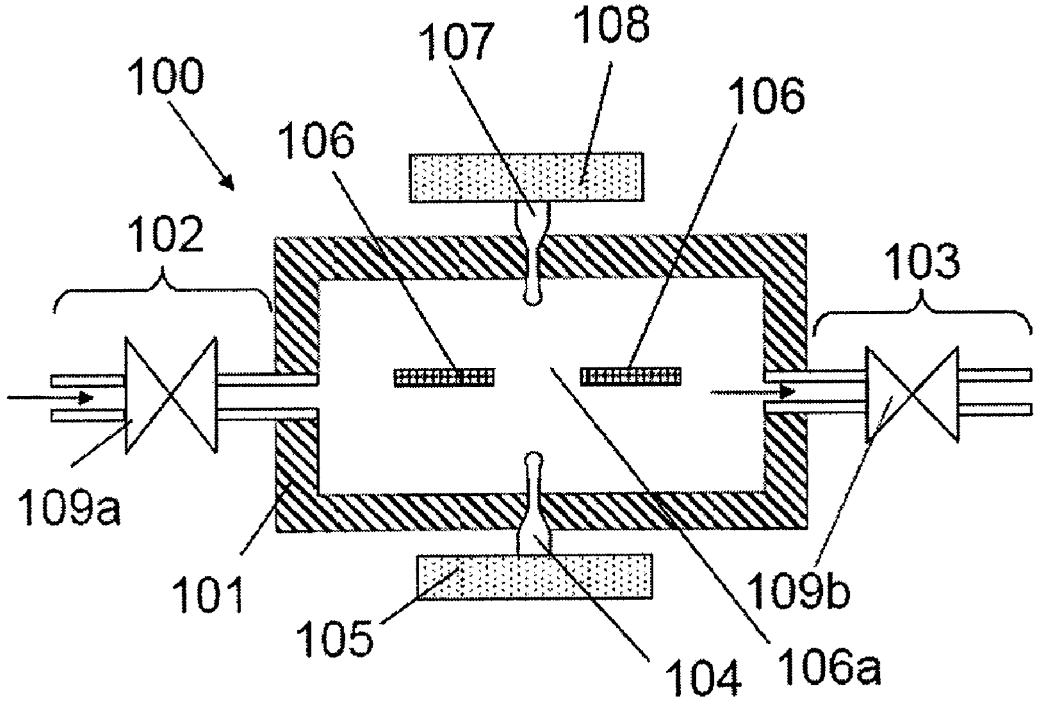

[Fig. 2]
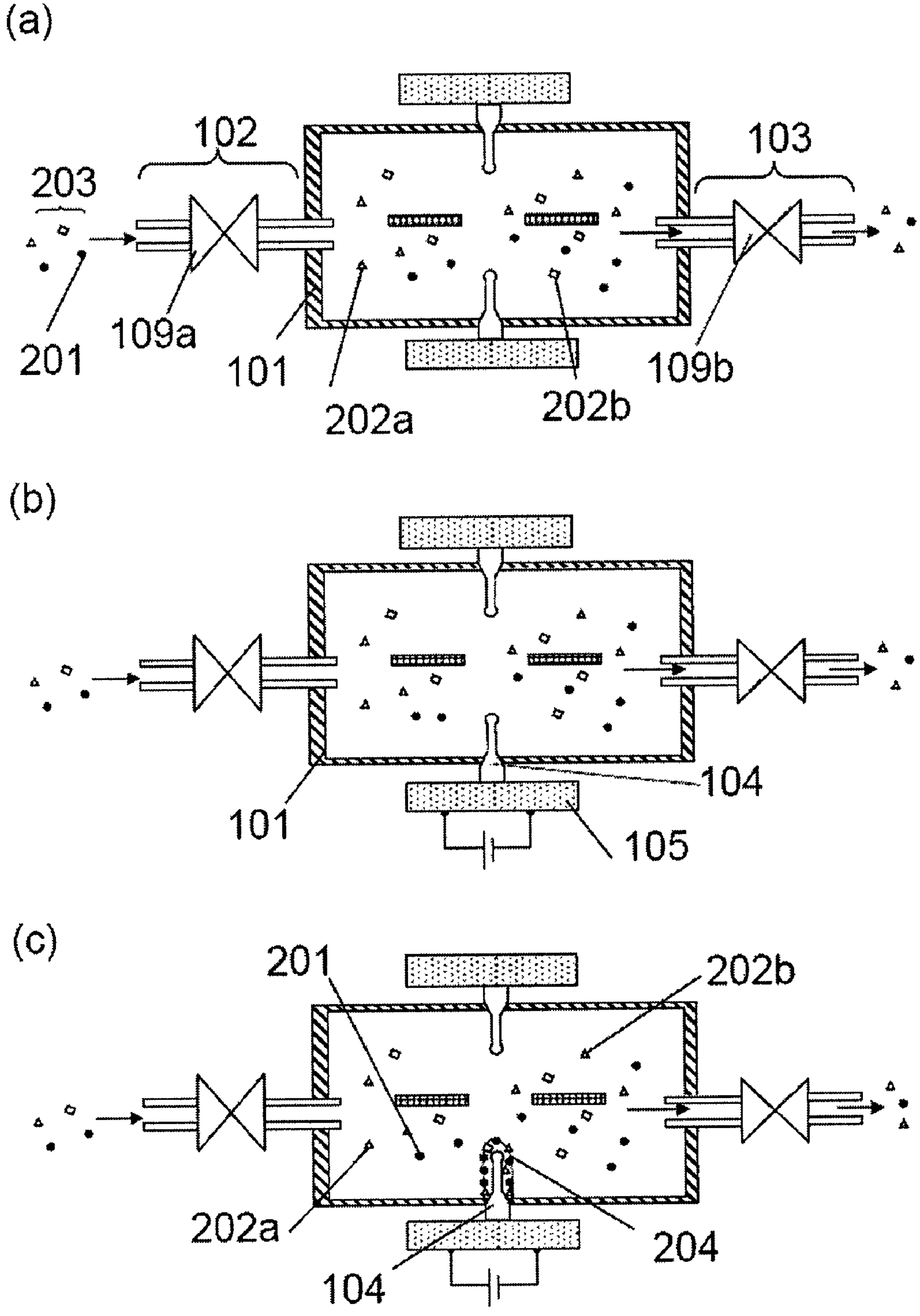

[Fig. 3]
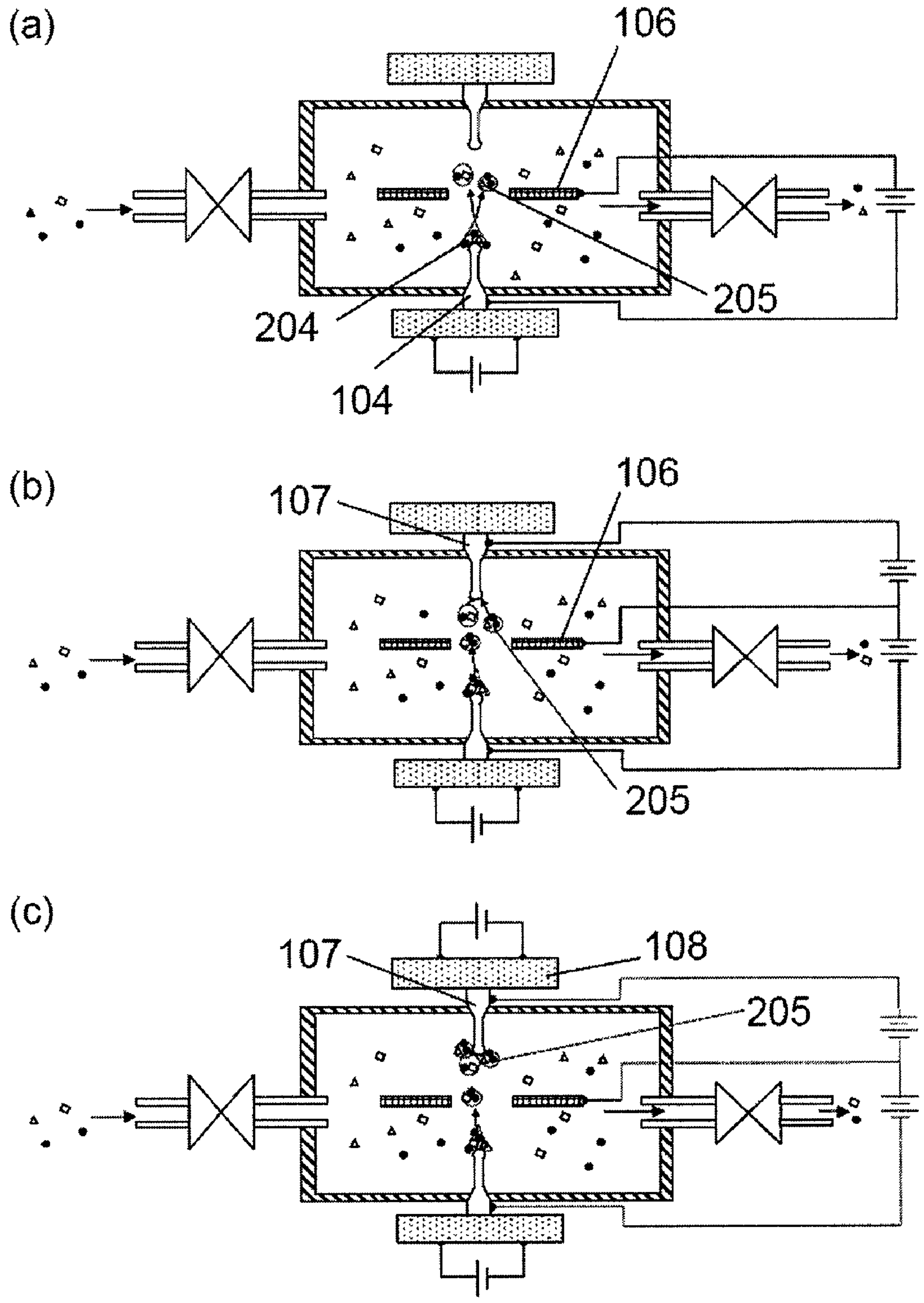

[Fig. 4]
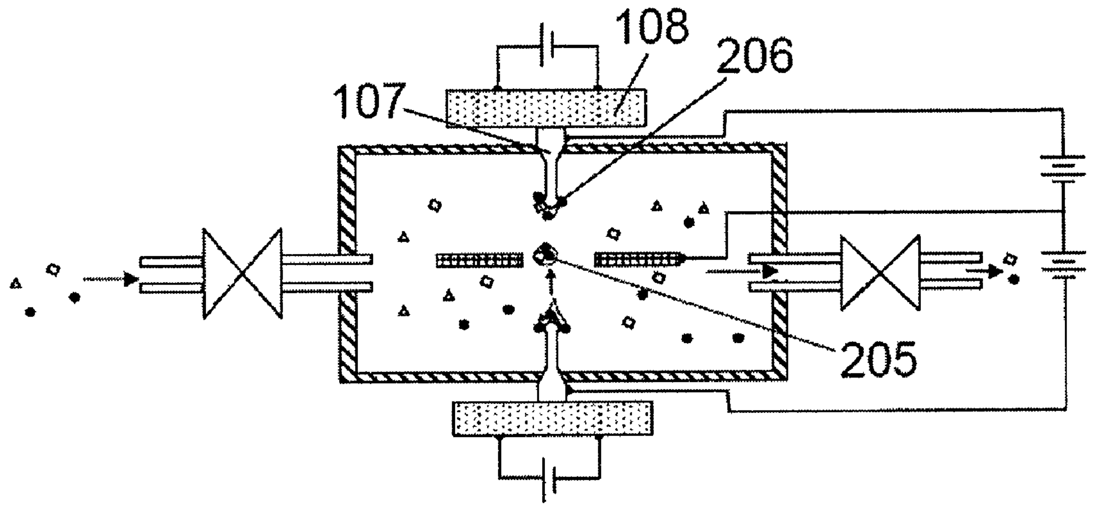

[Fig. 5]
(a)
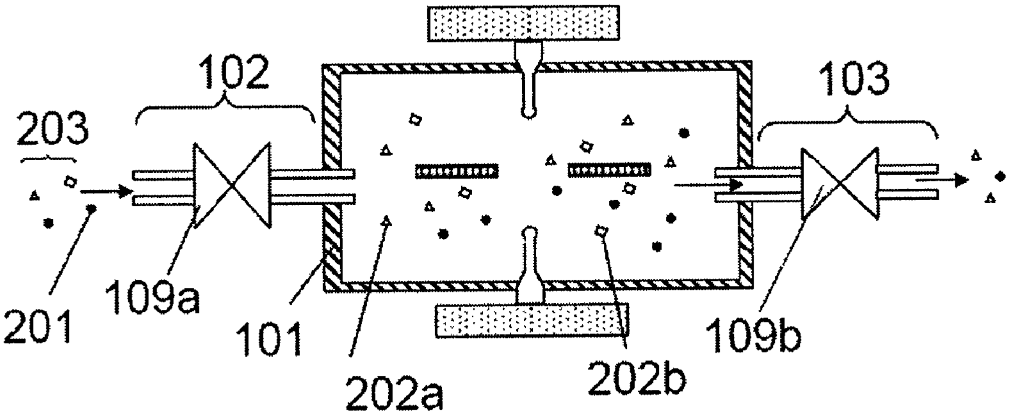
(b)
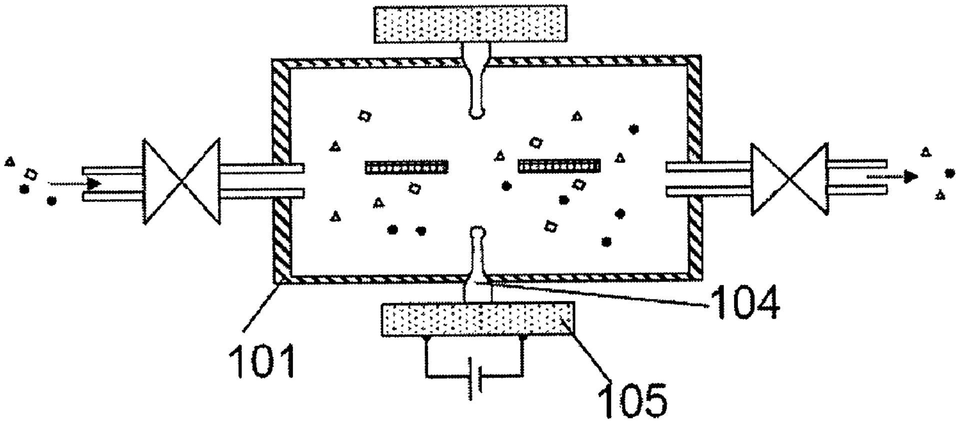
(c)
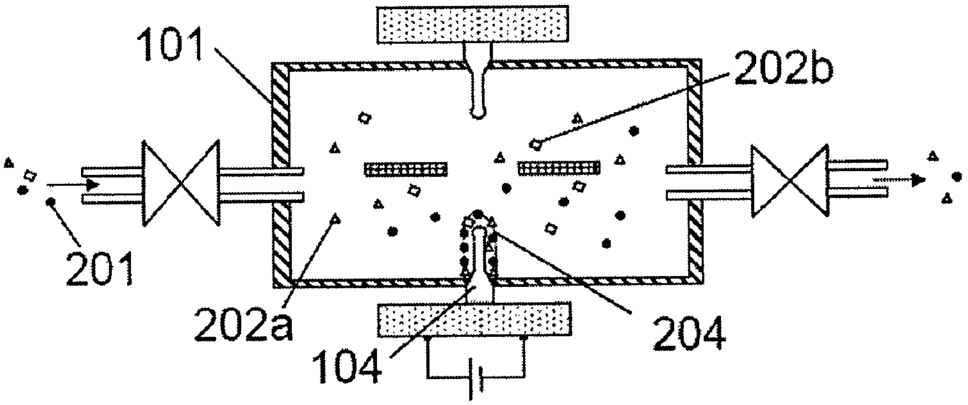

[Fig. 6]
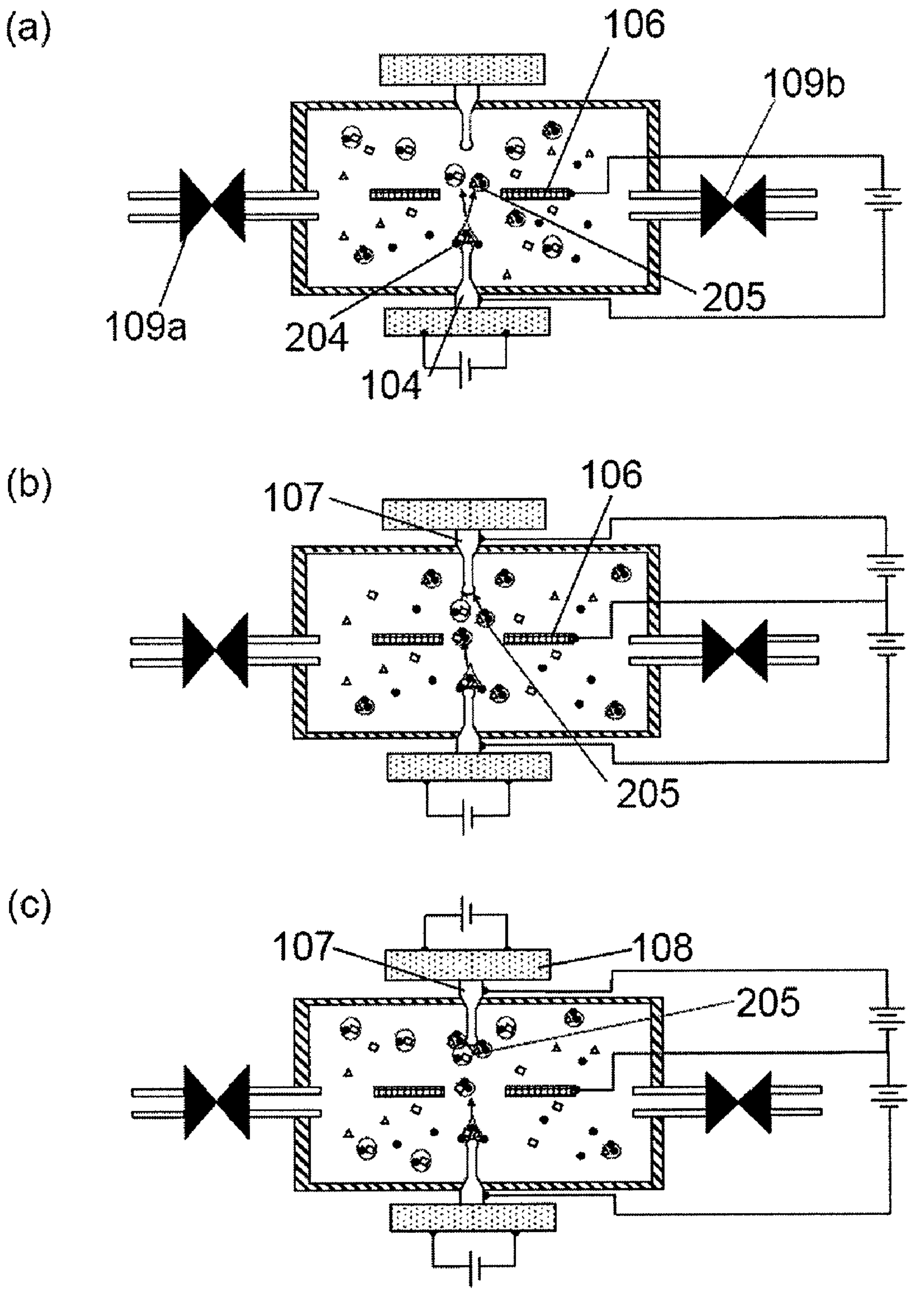

[Fig. 7]
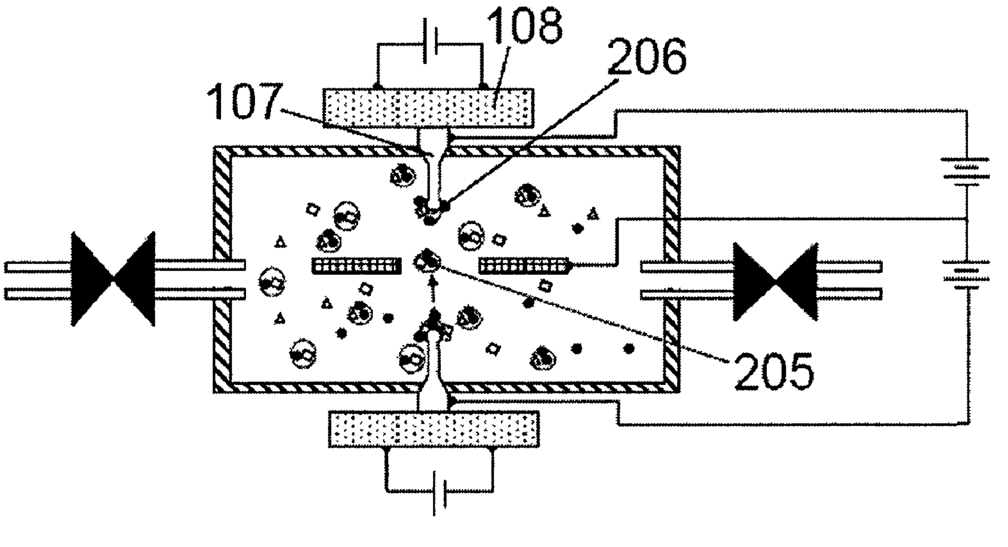

[Fig. 8]
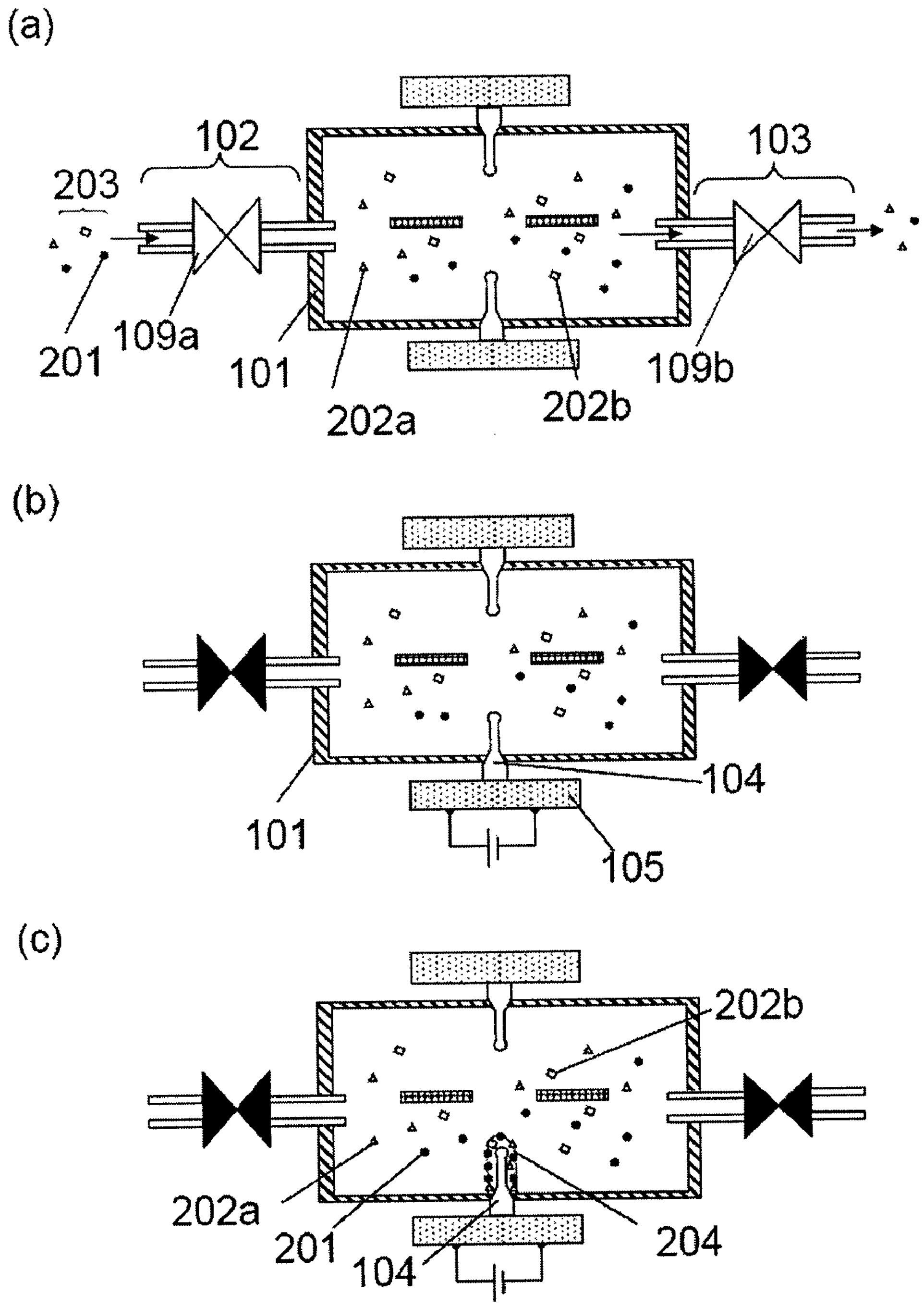

[Fig. 9]
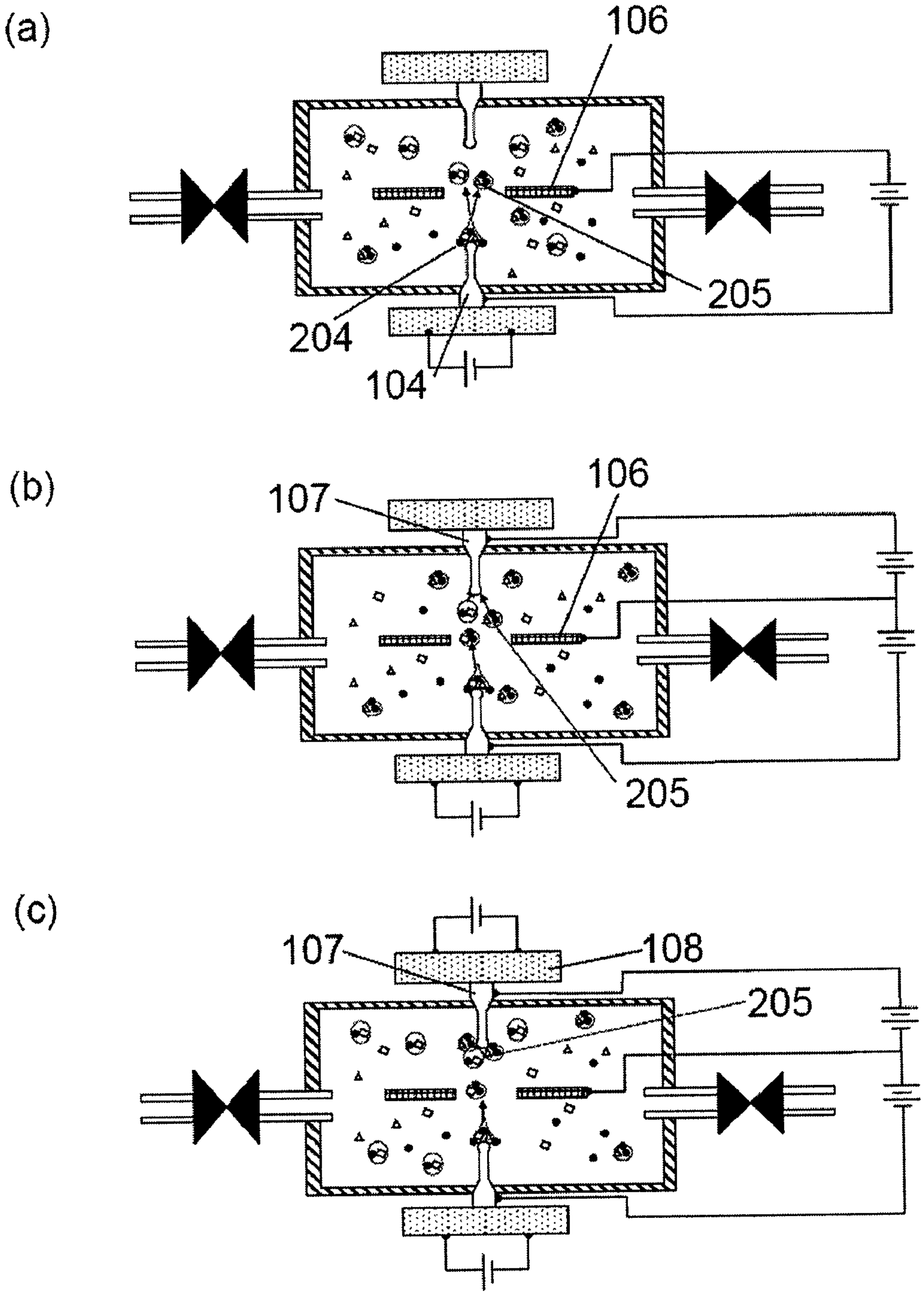

[Fig. 10]
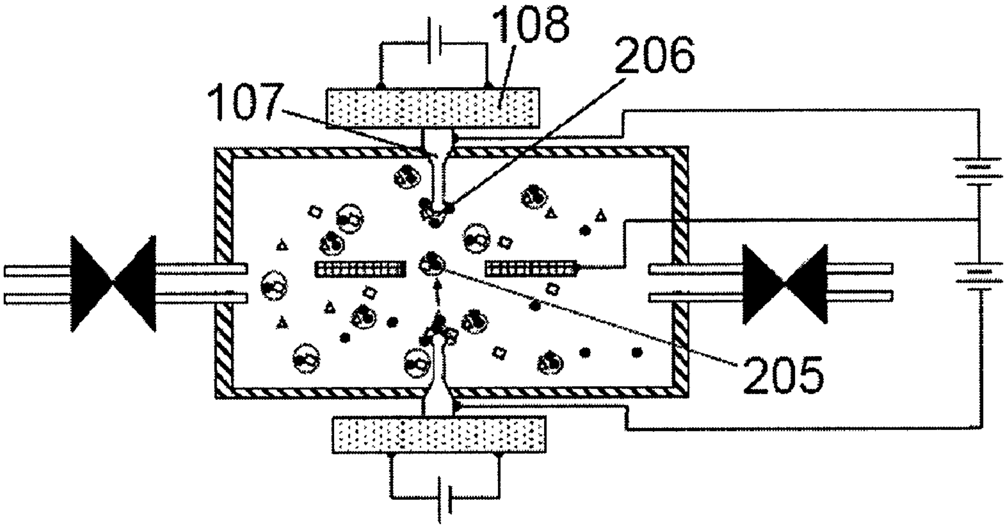

[Fig. 11]
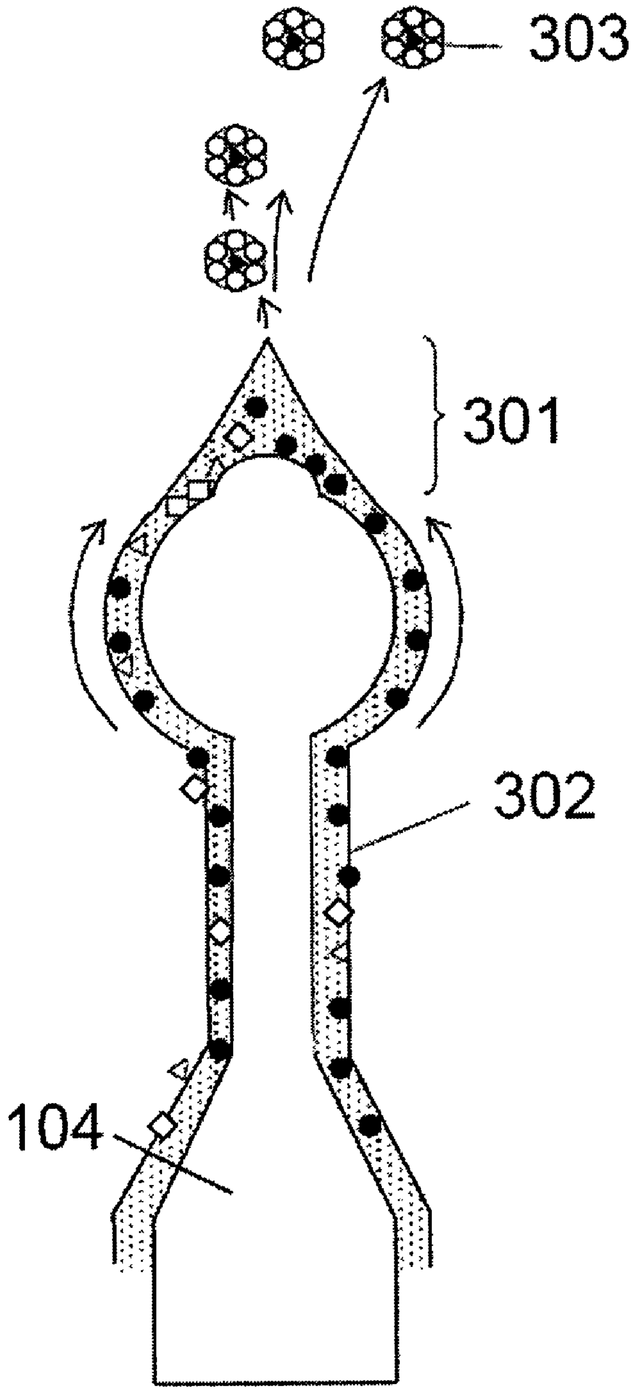

[Fig. 13]
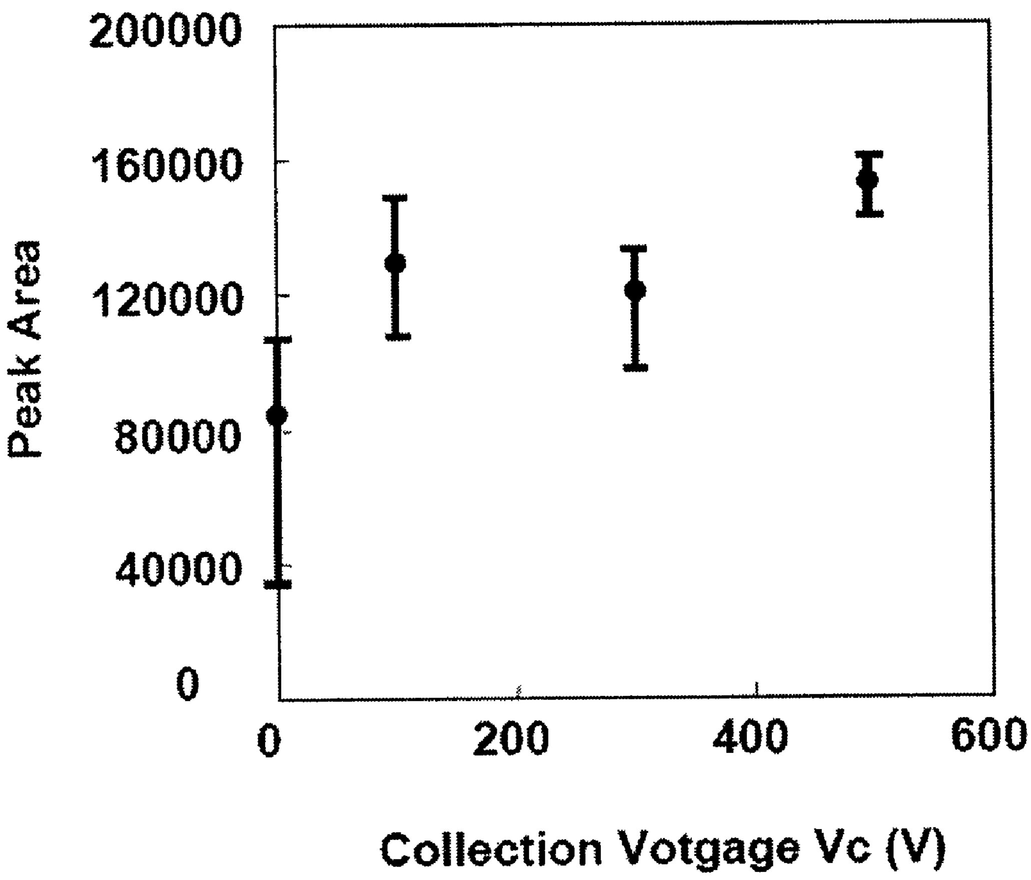

[Fig. 14] PRIOR ART
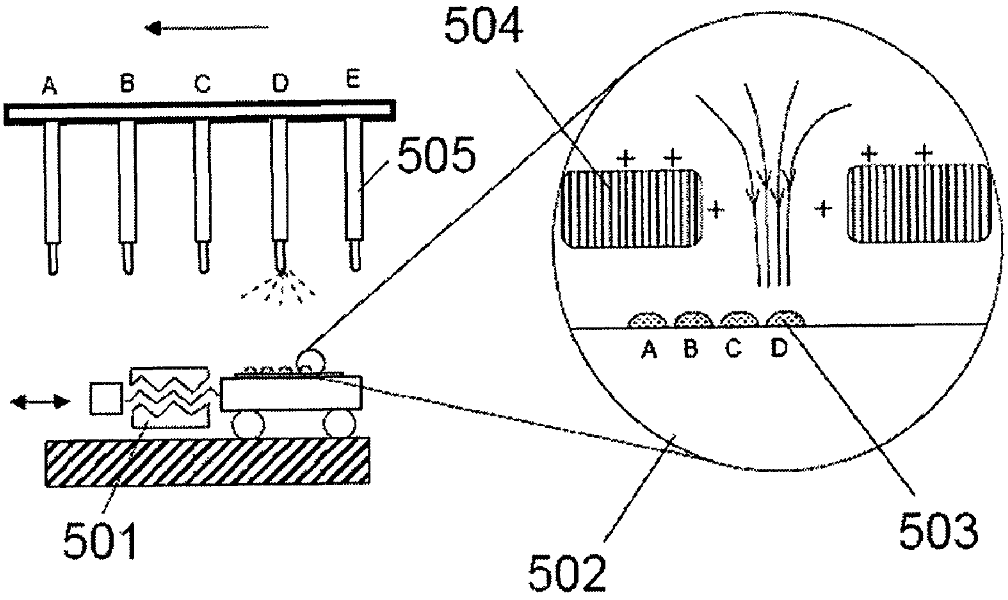

METHOD FOR COLLECTING GASEOUS SAMPLE

This application is a continuation of International Application No. PCT/JP2009/052255, whose international filing date is Feb. 4, 2009 which in turn claims the benefit of Japanese Patent Application No. 2008-024667, filed on Feb. 5, 2008, the disclosures of which Applications are incorporated by reference herein. The benefit of the filing and priority dates of the International and Japanese Applications is respectfully requested.

TECHNICAL FIELD

The present invention relates to a method for effectively collecting gaseous samples onto an electrode through electrostatic atomization.

BACKGROUND ART

Electrostatic atomization is well known in the art and has usually been used to accumulate onto base plates a trace amount of the various chemical substances like DNA, antibodies and proteins.

For example, the conventional electrostatic atomizer disclosed in Patent Publication 1 is an apparatus to spot or laminate onto base plates non-volatile diluted biomolecule solution. FIG. 14 illustrates the conventional electrostatic atomizer. By applying several kV of high-voltage between the capillary tubes 505 filled with protein solution and the dielectric layer 504, a mist of the protein solution is sprayed onto the base plate 502 from the tips of the capillary tubes 505.

Electrostatic atomizer illustrated in FIG. 14 accumulates any chemical solution at the desired positions 503 by controlling electrical conductivity in the dielectric layer 504 formed on the base plate 502 or generating a topical electric field with the hole at the dielectric layer 504. This method was certainly effective in the manufacture of those so called DNA chips or protein chips wherein DNA or protein is sequentially spotted or laminated onto base plates.

[Patent Citation 1]

Japanese Patent Provisional Publication No. 2002-511792 (Page 78, FIG. 9, and optionally Page 31, Lines 12-13, FIGS. 3, 4 and 19)

[Patent Citation 2]

Japanese Patent Publication No. 3952052

[Patent Citation 3]

Japanese Patent Provisional Publication No. 7-190990 (in particular FIG. 3)

[Patent Citation 4]

Japanese Patent Provisional Publication No. 7-270285 (in particular Paragraphs of 0001 and 0008)

DISCLOSURE OF INVENTION

Technical Problem

But when a capture electrode is made of a flat plate as taught by the prior art, electrostatically atomized solution is spread over the whole surface of such electrode.

Technical Solution

In order to eliminate such problems known in the art, the present disclosure is directed to a method for collecting a gaseous sample with an electrostatic atomizer, wherein the electrostatic atomizer comprises a sealable container, an inlet for the gaseous sample mounted at a part of the container, an outlet for the gaseous sample mounted at the other part of the container, an atomizing electrode mounted in the container, a primary refrigerator mounted adjacent to the atomizing electrode, an opposite electrode mounted in the container, an acicular capture electrode opposed to the opposite electrode, and a secondary refrigerator mounted adjacent to the capture electrode, and the method comprises the steps of introducing the gaseous sample into the container through the inlet, chilling the atomizing electrode with the primary refrigerator, preparing a primary condensate from the gaseous sample on an outer peripheral surface of the atomizing electrode, preparing charged microparticles from the primary condensate with electrostatic atomization, applying voltage to the capture electrode for the opposite electrode, chilling the capture electrode with the secondary refrigerator, and preparing a secondary condensate from the charged microparticles adjacent to the tip of the capture electrode.

It is preferable to complete the introduction of the gaseous sample on or before initiation of preparing charged microparticles.

Then, it is preferable to direct the tip of the capture electrode downwardly into the container.

Further, it is preferable to chill the capture electrode with the secondary refrigerator to the condensation point of water vapour or lower.

It is preferable to employ a thermoelectric element as the secondary refrigerator.

Further, it is preferable to change the chilling surface of the secondary refrigerator to a heating surface by reversing the polarity of direct voltage to be applied to the thermoelectric element.

It is preferable to evaporate the secondary condensate by heating said capture electrode.

Further, it is preferable that the temperature of the opposite electrode is maintained at the condensation point of water vapour or higher.

It is preferable that the charged microparticles comprise water and components of the gaseous sample.

Further, it is preferable that components of the gaseous sample are volatile organic compounds.

Further, it is preferable that the molecular weight of the volatile organic compounds is from 15 g/mol or more to 500 g/mol or less.

It is preferable that the capture electrode possesses a mechanism to remove electrical charge with the charged microparticles.

Further, it is preferable that the capture electrode is able to connect to ground.

It is preferable that the tip of the capture electrode has a reservoir to receive the secondary condensate.

Further, it is preferable that the tip of the capture electrode is equipped with a detector for chemical substances.

It is preferable that an apparatus to assay biomolecules employs a method for collecting gaseous sample.

These and other objects, additional aspects and advantages of the present disclosure will become apparent from the following detailed description on the preferred embodiments by referring to the drawings attached hereto.

Advantageous Effects

According to the method for collecting gaseous samples of the present disclosure, since electrostatically atomized solution is concentrated at an area adjacent to the tip of the acicular capture electrode, such electrostatically atomized solution does not spread over the capture electrode. Then, since the capture electrode is chilled by previously applying voltage to the capture electrode, such electrostatically atomized solution also does not spread over the capture electrode.

BRIEF DESCRIPTION OF DRAWINGS

FIG. 1 is an exemplary schematic view illustrating electrostatic atomizer according to Embodiment 1 of the present disclosure.

FIG. 2 is an exemplary schematic view illustrating a method for collecting a gaseous sample according to Embodiment 1 of the present disclosure.

FIG. 3 is an exemplary schematic view illustrating a method for collecting a gaseous sample according to Embodiment 1 of the present disclosure.

FIG. 4 is an exemplary schematic view illustrating a method for collecting a gaseous sample according to Embodiment 1 of the present disclosure.

FIG. 5 is an exemplary schematic view illustrating a method for collecting a gaseous sample according to Embodiment 2 of the present disclosure.

FIG. 6 is an exemplary schematic view illustrating a method for collecting a gaseous sample according to Embodiment 2 of the present disclosure.

FIG. 7 is an exemplary schematic view illustrating a method for collecting a gaseous sample according to Embodiment 2 of the present disclosure.

FIG. 8 is an exemplary schematic view illustrating a method for collecting a gaseous sample according to Embodiment 3 of the present disclosure.

FIG. 9 is an exemplary schematic view illustrating a method for collecting a gaseous sample according to Embodiment 3 of the present disclosure.

FIG. 10 is an exemplary schematic view illustrating a method for collecting a gaseous sample according to Embodiment 3 of the present disclosure.

FIG. 11 is an exemplary schematic view illustrating a tail cone and a method for producing charged microparticles.

FIG. 13 is a graph illustrating an assay results on the secondary condensate.

FIG. 14 is a schematic view illustrating the conventional electrostatic atomizer.

EXPLANATION OF REFERENCE

Detailed Description

Figure 12:
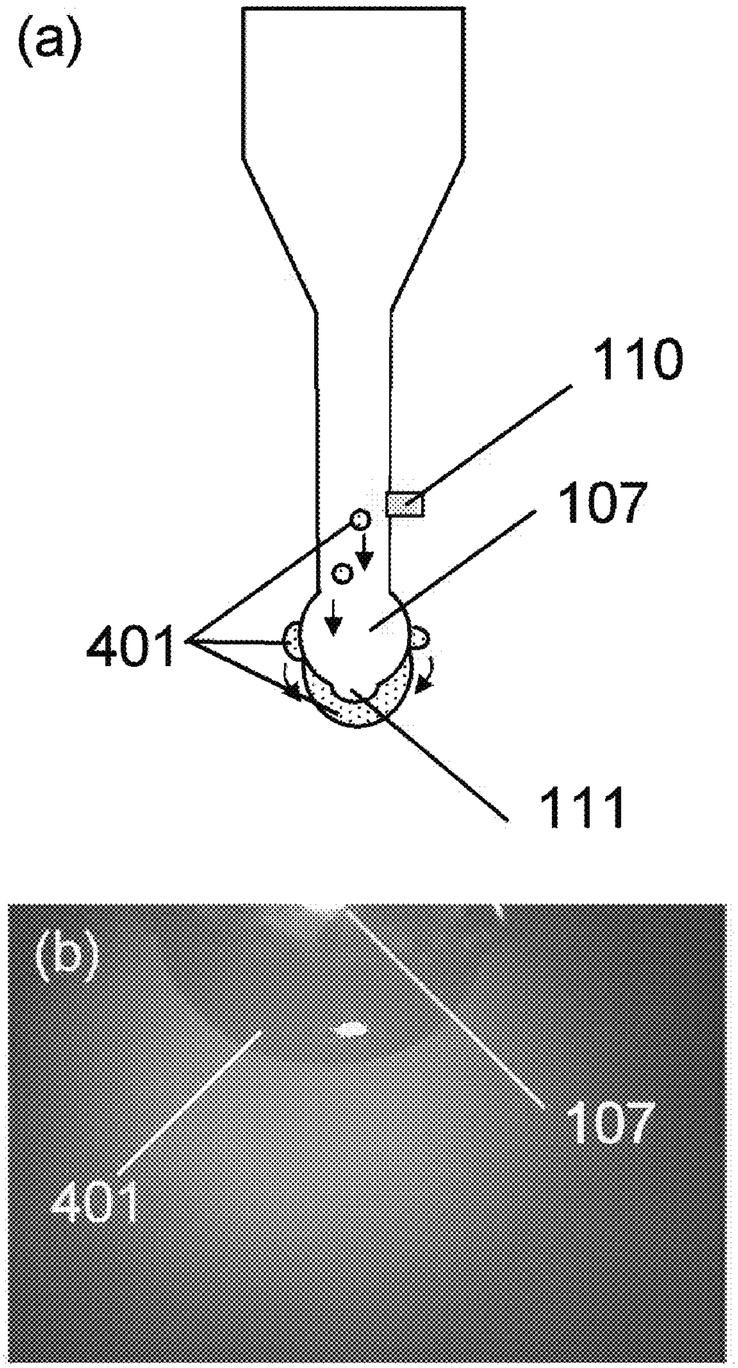
FIG. 12 is an exemplary schematic view illustrating the capture electrode 107 at the step of preparing secondary condensate and a photograph thereon taken by a light microscope.

Embodiments of the present disclosure are described as follows with reference to the drawings attached hereto.

Embodiment 1

FIG. 1 is an exemplary schematic view illustrating a electrostatic atomizer according to Embodiment 1 of the present disclosure.

According to this embodiment, the electrostatic atomizer 100 is assembled from the following elements.

Container 101 is isolated from the outside thereof with a partition. The shape of the container 101 may preferably be, but not limited to, rectangular parallelepiped form, polyhedron form, spindle form, spherical form or channel form. Then, with regard to the size of the container 101, the volume of the container 101 should preferably be sufficiently less than the total amount of the gaseous sample to be introduced. For example, when 300 cc of the gaseous sample as the total amount thereof is introduced, the volume of the container should preferably be 6 cc or less. Further, materials for the container 101 are preferably those which have less adsorbed gas or incorporated gas. As such, metal like stainless steel or aluminum is the most preferable, but inorganic materials like glass or silicon or plastics like acryl, polyethylene terephthalate or Teflon (Registered Trademark) may also be used. The container can also be made by employing some of these materials. In the meantime, the container 101 is preferable a hard structure, but it may be soft or flexible, such as, an airbag, balloon, flexible tube or syringe.

Inlet 102 is mounted at a part of the container 101. Inlet 102 is used to introduce the gaseous sample into the container 101. As the position for the inlet 102 to be mounted, any position can be used as long as it allows rapidly introducing the gaseous sample into the container 101. For example, when the shape of the container 101 is a rectangular parallelepiped form, the inlet should preferably be mounted at the center of the surface in the container 101 rather than the corner thereof. Shape, size and material of the inlet 102 are not limited in the present disclosure. As a shape of the inlet 102, the linear form like that indicated in FIG. 1 or the other linear form comprising a branched space may be used. Further, one or more inlets 102 may be mounted to the container.

Outlet 103 is mounted at another part of the container 101. Outlet 103 is used to exhaust the excessive gaseous sample, which saturate the container 101. As a position for the outlet 103 to be mounted, any position can be used as long as it allows exhausting the excessive gaseous sample of those which saturate the container 101. Shape, size and material of the outlet 103 are not limited in the present disclosure. As a shape of the outlet 103, the linear form like that indicated in FIG. 1 or the other linear form comprising a branched space may be used. Further, one or more outlets 103 may be mounted to the container.

Atomizing electrode 104 is mounted in the container 101. Atomizing electrode 104 is preferably mounted at a position where it is in the container 101 and can be in contact with the gaseous sample. For example, it is preferably mounted at the center of the bottom of the container 101. Minimizing the contact area between the atomizing electrode 104 and the container 101 is preferable in view of reducing thermal conductivity.

The shape of the atomizing electrode 104 is preferably acicular in form. Length of the acicular electrode is preferably from 3 mm or more to 10 mm or less. The diameter of the acicular electrode is preferably from 0.5 mm or more to 1.0 mm or less. The diameter may be the same from the tip of the electrode to the root thereof. Alternatively, it may be uneven by reducing the diameter of the tip portion and maintaining that of the root portion (i.e., the diameter narrows as the distance from the root portion increases). One or more acicular electrodes may be mounted in the container.

Further, as materials for the atomizing electrode 104, good thermal conductive materials are preferable, in particular, metal is the most preferable. Especially, uncompounded metal like stainless steel, copper, brass, aluminum, nickel or tungsten may be used, otherwise, an alloy or an intermetallic compound made from two or more of the foregoing uncompounded metals may also be used. Further, in order to protect the surface of the atomizing electrode 104, the electrode 104 may be coated with a film of chemically stable metal, such as, gold or platinum or with the other good thermal conductive materials.

Primary refrigerator 105 is mounted adjacent to the atomizing electrode 104. Primary refrigerator 105 chills the atomizing electrode 104. It is preferable that the primary refrigerator 105 is a thermoelectric element, but any heat pipe employing refrigerant carrier like water, air heat exchange element or cooling fan may also be used. Larger surface area to be chilled in the primary refrigerator 105 can effectively chill the atomizing electrode 104. Accordingly, the size of the primary refrigerator 105 may be adjusted to realize the maximum contact area between that and the atomizing electrode 104, outer peripheral surface to be chilled in the primary refrigerator 105 may have rough structure, otherwise, the outer peripheral surface to be chilled in the primary refrigerator 105 may have porous structure. One or more the primary refrigerator 105 may be used.

In the meantime, the primary refrigerator 105 preferably contacts with the atomizing electrode 104 directly, but it may also contact the electrode 104 through a thermal conductive medium like thermal conductive sheet, thermal conductive resin, metal plate or grease. Then, the primary refrigerator 105 preferably contacts with the atomizing electrode 104, but it may be separated occasionally therefrom with physical or thermal means.

Opposite electrode 106 is opposite to the atomizing electrode 104. Opposite electrode 106 is used for electrostatic atomization in combination with the atomizing electrode 104. The distance between the opposite electrode 106 and the tip of the atomizing electrode 104 is preferably from 3 mm or more to 4 mm or less. Toric shape is the most preferable for the opposite electrode 106. FIG. 1 illustrates the sectional view of the toric opposite electrode 106. It is most preferable to place the center of the toric opposite electrode 106 onto the production of the acicular atomizing electrode 104 (i.e., centered about the vertical axis of the electrode 104). The shape of the opposite electrode 106 may be any polygon like rectangle or trapezoid. In addition, slit 106*a* like through holes, wherein the charged microparticles are passed through, may be formed in the opposite electrode 106. The thickness of the opposite electrode 106 is not limited in the present disclosure. Further, the sectional area, the shape and the amount of the through holes are not limited in the opposite electrode in the present disclosure.

Metal is preferable as the material for the opposite electrode 106. Especially, uncompounded metal like iron, copper, zinc, chromium, aluminum, nickel or tungsten may be used, in addition, an alloy like stainless steel or brass, or an intermetallic compound comprising two or more of the foregoing uncompounded metals may also be used. Further, in order to protect the surface of the opposite electrode 106, the opposite electrode may be coated with a film of chemically stable metal like gold or platinum or with the other good thermal conductive materials.

Capture electrode 107 is mounted adjacent to the opposite electrode 106. The opposite electrode 106 is preferably mounted between the capture electrode 107 and the atomizing electrode 104. Further through holes in the capture electrode 107 and the opposite electrode 106 are preferably aligned substantially linear with the atomizing electrode 104. Capture electrode 107 is preferably mounted at the ceiling of the container 101, the atomizing electrode 104 is preferably mounted at the bottom of the container 101, and the opposite electrode 106 is preferably mounted between the capture electrode 107 and the atomizing electrode 104. Capture electrode 107 is used to collect electrostatically atomized charged microparticles with static electricity.

The shape of the capture electrode 107 is preferably acicular form. The length of the acicular electrode is preferably from 3 mm or more to 10 mm or less. The diameter of the acicular electrode is preferably from 0.5 mm or more to 1.0 mm or less. The diameter may be the same from tip of the electrode to the root thereof. Alternatively, it may be uneven by reducing the diameter of the tip portion and maintaining that of the root portion (i.e., the diameter narrows as the distance from the root portion increases). The distance between the tip of the capture electrode 107 and the opposite electrode 106 is not limited in the present disclosure. Further, as materials for the capture electrode 107, good thermal conductive materials are preferable, in particular, metal is the most preferable. Especially, uncompounded metal like iron, copper, zinc, chromium, aluminum, nickel or tungsten may be used, in addition, an alloy like stainless steel or brass, or an intermetallic compound comprising two or more of the foregoing uncompounded metals may also be used. Further, in order to protect the surface of the capture electrode 107, the capture electrode 107 may be coated with a film of chemically stable metal, such as, gold or platinum or with the other good thermal conductive materials.

Further, since the electrical field is preferably concentrated at the tip of the capture electrode 107, the shape of the capture electrode may be formed in a conical shape, square pyramid or trigonal pyramid, or otherwise in some other sharp shape. Most preferably acicular capture electrode 107 is solid, but it may be hollow, such as, a pipe. One or more the capture electrodes 107 may be used.

Further, the tip of the capture electrode 107 is preferably mounted so as to extend downwardly into the container. As such, the electrostatically atomized solution tends to move toward the tip due to gravity.

Secondary refrigerator 108 is mounted adjacent to the capture electrode 107. Secondary refrigerator 108 is used to chill the capture electrode 107. Most preferably the secondary refrigerator 108 is a thermoelectric element, but any heat pipe employing refrigerant carrier like water, air heat exchange element and cooling fan may also be used. Larger surface area to be chilled in the secondary refrigerator 108 can effectively chill the capture electrode 107. Accordingly, the size of the secondary refrigerator 108 may be adjusted to realize the maximum contact area between that and the capture electrode 107. The outer peripheral surface to be chilled in the secondary refrigerator 108 may have a rough structure, otherwise, the outer peripheral surface to be chilled in the secondary refrigerator 108 may have a porous structure. One or more the secondary refrigerators 108 may be used.

The secondary refrigerator 108 preferably contacts the capture electrode 107 directly, but it may also contact the capture electrode 107 through a thermal conductive medium like a thermal conductive sheet, a thermal conductive resin, a metal plate or grease. The, the secondary refrigerator 108 preferably contacts the capture electrode 107 usually, but it may be separated occasionally therefrom with physical or thermal means.

Although it is most preferable for the secondary refrigerator 108 and the primary refrigerator 105 to be controlled individually, a single refrigerator may be used as both the primary refrigerator 105 and the secondary refrigerator 108. Size, kind and amount of the primary refrigerator 105 may be identical to or be different from those of the secondary 108 refrigerator.

Valves 109*a* and 109*b* are preferably mounted at the inlet 102 and the outlet 103. Container 101 can preferably be sealed with such valves 109*a* and 109*b*. Materials, position and kinds of the valves 109*a* and 109*b* are not limited in the present disclosure. Further, when conductance of the valves 109*a* and 109*b* is minimal, the container 101 is regarded as essentially sealed.

FIGS. 2-4 are exemplary schematic views illustrating a method for collecting the gaseous sample according to Embodiment 1 of the present disclosure. The same symbols were allocated to the elements in FIGS. 2-4 according to the corresponding identical elements in FIG. 1 and any description of such elements has been omitted.

First of all, the gaseous sample 203 consisting of water 201 and chemical substance 202*a*, 202*b* is introduced into the container 101 through the inlet 102. FIG. 2 (*a*) illustrates introducing a gaseous sample. A gaseous sample detector may be mounted in the container 101 to confirm whether or not the container 101 is filled with the gaseous sample 203. One or more gaseous sample detectors can be mounted. According to the present disclosure, any kind and position of the gaseous sample detector can be employed.

During introduction of the gaseous sample, the gaseous sample 203 is preferably placed into the container 101 from the inlet 102, though the gaseous sample may also be placed into the container by depressurizing the outlet 103.

Further, during introduction of the gaseous sample, prior to introducing of the gaseous sample 203 into the container 101, the container 101 is preferably filled with fresh air. Container 101 may be filled with dry nitrogen gas or other inactive gas, otherwise it may be filled with standard gas or calibration gas where their humidity is equivalent to that of the gaseous sample.

Then, during introduction of the gaseous sample, excessive gaseous sample 203 is exhausted through outlet 103.

Introduction and exhaustion of the gaseous sample 203 during the introduction of the gaseous sample are controlled by the valve 109*a* and the valve 109*b*. A trap may be mounted at the inlet 102 so as not to introduce unnecessary products.

For convenience sake, FIG. 2 (*a*) does not include any substance except for chemical substances 202*a*, 202*b*, but the gaseous sample 203 may includes two or more components.

Then, during production of the primary condensate, the atomizing electrode 104 is chilled by the primary refrigerator 105. FIG. 2 (*b*) illustrates production of the primary condensate. According to FIG. 2 (*b*), the primary refrigerator 105 is connected to direct power to illustrate an image of chilling the atomizing electrode 104 by the primary refrigerator 105. But the present disclosure is not limited to such direct power on the primary refrigerator 105 during production of the primary condensate.

By producing the primary condensate after such introduction of the gaseous sample, any condensation on all the substances except for such gaseous sample can be controlled. During production of the primary condensate, it is preferable to decrease the thermal conductivity so as not to chill any part except for the atomizing electrode 104, for example, the container 101. In order to decrease the thermal conductivity, it is most preferable to reduce the contact area between the atomizing electrode 104 and the container 101. Otherwise, any material having a lower coefficient of thermal conductivity may be disposed at the contact space between the atomizing electrode 104 and the container 101.

Then, during production of the primary condensate, the primary condensate 204 comprising water 201, the chemical substance 202*a* and the chemical substance 202*b* are formed on the outer peripheral surface of the chilled atomizing electrode 104. FIG. 2 (*c*) illustrates the producing of the primary condensate.

During production of the primary condensate, it is preferable to control the temperature of the atomizing electrode 104 with the primary refrigerator 105 so as to not generate an excess amount of the primary condensate 204.

Then, during production of the charged microparticles, numerous charged microparticles 205 are formed from the primary condensate 204. FIG. 3 (*a*) illustrates producing the charged microparticles. Such charged microparticles are most preferably microparticles consisting of several thousand molecules, but they may be single through several hundred of clusters or be several ten thousand liquid droplets. Two or more of those may be used simultaneously.

Charged microparticles 205 may also include ions or radicals from chemical substances in addition to electrically neutral molecules. They may be used simultaneously. Charged microparticles 205 are preferably charged negatively, but they may be charged positively.

The most preferable method to produce the charged microparticles is an electrostatic atomization. The principle of the electrostatic atomization is briefly noted herein. Primary condensate 204 is transferred to the tip of the atomizing electrode 104 by the voltage applied between the atomizing electrode 104 and the opposite electrode 106. The liquid level of the primary condensate 204 is conically raised toward the opposite electrode 106 by coulomb attraction. Such conically raised liquid is called a Taylor cone. When the condensate is further grown at the outer peripheral surface of the atomizing electrode 104, the conical primary condensate 204 is also grown and electrical charges are concentrated at the tip of the primary condensate 204, thereby, such coulomb attraction is enhanced. When such coulomb attraction is in excess of the surface tension of water, the primary condensates 204 are broken and dispersed, then the charged microparticles 205 are formed. This is the principle of the electrostatic atomization.

During production of the charged microparticles, a voltage of from 4 kV or more to 6 kV or less is preferably applied between the atomizing electrode 104 and the opposite electrode 106.

The diameter of the charged microparticles 205 is not particularly limited according to the present disclosure, but it is preferably restricted to the range of from 2 nm or more to 30 nm or less in view of stability of the charged microparticles.

An electrical amount to be charged to the charged microparticles 205 is most preferably an amount equivalent to the electrical charge content ($1.6\times10^{-19}$ C) per the single microparticle, but such amount can be changed to that larger than the electrical charge content.

Then, during application of the voltage, the voltage is applied to the capture electrode 107 for the opposite electrode 106. FIG. 3 (*b*) illustrates application of the voltage. Charged microparticles 205 having the diameter of from about 2 nm to about 30 nm tend to be dispersed because they are repulsed by static electricity, but most of the charged microparticles 205 are easily concentrated adjacent to the tip of the capture electrode 107 by providing the acicular capture electrode 107 and concentrating static electricity thereto. When the charged microparticles 205 are negatively charged, it is preferable to apply direct positive voltage to the capture electrode 107 for the opposite electrode 106. Application of the voltage is preferably continuous, but it may also be applied in a pulsed mode.

Then, during production of the secondary condensate, the capture electrode 107 is chilled by the secondary refrigerator 108. FIG. 3 (*c*) illustrates production of the secondary condensate. By producing the secondary condensate after such application of voltage, charged microparticles 205 are concentrated adjacent to the tip of the capture electrode 107 and can be chilled.

Then, during production of the secondary condensate, most of the charged microparticles 205 are condensed adjacent to the tip of the capture electrode 107, then the secondary condensates 206 are formed. FIG. 4 illustrates producing the secondary condensate. As a result of producing the secondary condensate, it prevents the capture electrode 107 from spreading the secondary condensate 206 on the whole surface thereof.

According to the embodiment of the present disclosure, it is preferable to chill the capture electrode 107 with the secondary refrigerator 108 to the condensation point of water vapour or lower. The temperature of the capture electrode 107 may be measured with a thermometer mounted adjacent to the capture electrode 107. Temperature of the capture electrode 107 may also be controlled.

Then, according to the embodiment of the present disclosure, it is preferable to heat the capture electrode 107 to evaporate the secondary condensate 206. The temperature of the heated capture electrode 107 is preferably the condensation point of water vapour or higher. Thereby, the gaseous sample is not condensed on the capture electrode 107 at unwanted times.

Further, according to the embodiment of the present disclosure, it is preferable to change the surface to be chilled in the secondary refrigerator 108 into the heating surface by reversing the polarity of the voltage to be applied to the thermoelectric element. Thereby, since the capture electrode 107 can be heated, the secondary condensate 206 can be easily evaporated.

According to the embodiment of the present disclosure, it is preferable to maintain the temperature of the opposite electrode 106 at the condensation point of water vapour or higher. By maintaining the temperature of the opposite electrode 106 at the condensation point of water vapour or higher, the charged microparticles 205 would not be condensed on the outer peripheral surface of the opposite electrode 106. In order to maintain the temperature of the opposite electrode 106 at the condensation point of water vapour or more, any heating unit may be mounted at the opposite electrode 106.

Charged microparticles 205 preferably comprise water 201 together with the chemical substances 202*a*, 202*b* which are components of the gaseous sample. The weight ratio of water and the gaseous sample components in the charged microparticles may be identical to that of water and gaseous sample components in the gaseous sample or may be different therefrom.

Then, according to the embodiment of the present disclosure, the component of the gaseous sample is preferably volatile organic compounds (particularly, volatile organic compounds having a molecular weight of from 15 g/mol or more to 500 g/mol or less). Such volatile organic compounds may preferably include ketone, amine, alcohol, aromatic hydrocarbon, aldehyde, ester, organic acid, hydrogen sulfide, methyl mercaptan and disulfide. Otherwise, these substances or alkane, alkene, alkyne, diene, cycloaliphatic hydrocarbon, allene, ether, carbonyl, carbanion, protein, polynuclear aromatic, heterocyclic, organic derivative, biomolecule, metabolite, isoprene, isoprenoid and derivative thereof may also be used.

Further, according to the embodiment of the present disclosure, the capture electrode 107 is preferably destaticized. For example, when the charged microparticles 205 are charged negatively, the capture electrode 107 will also be charged negatively according to gaseous sample components collected at capture electrode 107. Since it will be difficult to collect the charged microparticles 205 adjacent to the tip of the capture electrode 107 when the charged amounts thereof are excessive, any destaticization system should preferably be provided. Such destaticization may be conducted continuously or optionally.

According to the embodiment of the present disclosure, the capture electrode 107 is preferable able to connect to ground to destaticize (i.e., electrically neutralize) the capture electrode. Any connection method for connecting the capture electrode 107 to ground can be employed in the present disclosure.

Further, according to the embodiment of the present disclosure, it is preferable to provide a reservoir 110 to store the secondary condensate 206 at the tip of the capture electrode 107. By providing the reservoir 110 at the tip of the capture electrode 107, the secondary condensate 206 does not spread over the whole surface of the capture electrode 107. The reservoir may have a rough structure at the tip of the capture electrode 107. By providing such a rough structure, the contact area between the structure and the secondary condensate 206 is increased, thereby the liquid is stored therein. The shape of the reservoir 110 may include, but is not limited to, a globular form, a spindle form, and other polygonal forms. When the reservoir 110 is in the shape of a globular form, the diameter thereof is preferably in the range of from 1 mm or more to 2 mm or less. The reservoir 110 may comprise any water absorbent, such as, porous material, nanofoam and gel. The outer peripheral surface of the tip of the capture electrode 107 may also be subjected to hydrophilic treatment. As such a hydrophilic treatment, hydrophilic materials like glass and titanium oxide may be formed into a film. Alternatively, any organic molecule having hydrophilic group like silanol group, carboxyl group, amino group and phosphoric group at the terminal thereof may be absorbed or be bound.

Further, according to the embodiment of the present disclosure, it is preferable to provide a chemical substance detector 111 at the tip of the capture electrode 107. As such a chemical substance detector 111, in addition to a gas chromatograph, other chemical substance detectors may also be utilized. For example, a sensor like MOSFET (Metal-Oxide-Semiconductor Electric Field Transistor), ISFET (Ion Sensitive Electric Field Transistor), Bipolar Transistor, Organic Thin Layer Transistor, OPTODE, Metal Oxide Semiconductor Sensor, Quartz Crystal Microbalance (QCM), Surface Acoustic Wave (SAW) Element, Solid Electrolyte Gas Sensor, Electrochemical Cell Sensor, Surface Wave Plasmon Resonance (SPR), Langmuir-Blodgett Film (LB Film) Sensor may be used. Alternatively, High Performance Liquid Chromatograph, Mass Spectrometer, Nuclear Magnetic Resonance Spectrometer, LC-IT-TOFMS, SHIFT-MS may also be used. In addition, one or more chemical substance detectors may be mounted in the container. Further, when two or more chemical substance detectors are used, a single type of the detector may be used, while multiple types thereof may also be used in combination with one another. Any acceptable means for transferring the secondary condensate 206 between the capture electrode 107 and the chemical substance detector may be provided.

According to the embodiment of the present disclosure, an assay apparatus for biomolecules may employ the present method for collecting the gaseous sample. Such biomolecules preferably include ketone, amine, alcohol, aromatic hydrocarbon, aldehyde, ester, organic acid, hydrogen sulfide, methyl mercaptan and disulfide. Alternatively, alkane, alkene, alkyne, diene, cycloaliphatic hydrocarbon, allene, ether, carbonyl, carbanion, protein, polynuclear aromatic, heterocyclic, organic derivative, biomolecule, metabolite, isoprene, isoprenoid and derivatives thereof may also be used. Other biological organic compounds may also be utilized.

According to the embodiment of the present disclosure, the charged microparticles 205 are concentrated adjacent to the tip of the acicular capture electrode 107 during application of a voltage to prevent condensate from spreading at an electrode to capture it and are chilled secondary, thereby, the secondary condensate 206 are duly produced. Concentration of the secondary condensate 206 to be realized by secondary chilling of the charged microparticles after application of voltage is larger than that to be realized by secondary chilling the charged microparticles prior to application of voltage.

It is noted that the present embodiment is quite different from the conventional generator for negatively charged mist relied on electrostatic atomization. Namely, the diameter of charged microparticles produced by such a conventional mist generator is very small and is in a range of from several nm to several ten nm. Charged microparticles in nanometer size tend to (1) float in air for the longer periods of about 10 minutes and (2) easily spread. Such properties in the negatively charged mist are advantageous in a humectant apparatus or deodorant apparatus for skin and hair. But such properties are disadvantageous when collecting the chemical substances according to the present disclosure. Accordingly, prior to the present disclosure, there has been no reason to use an electrostatic atomization method which produces the charged microparticles in nanometer size to collect the chemical substances. However, by utilizing the method of this embodiment, such chemical substances can be effectively captured, even if the charged microparticles in nanometer size tend to float or spread.

Further, according to the embodiment of the present disclosure, the container 101 is made of plastics, Teflon (Registered Trademark) is the most preferable, while acrylic resin, polyethylene terephthalate (PET), polyester, fluorine plastics or PDMS may also be used. When the container 101 is made of plastic, it is more preferable to coat a metallic film onto the inner surface of the container 101. As such a metallic film, aluminum film is the most preferable in view of its lower cost and its ideal gas barrier properties, but the other metallic films may also be used. Further, two or more of such metal films may be used simultaneously.

According to the embodiment of the present disclosure, when the container 101 is made of inorganic materials, any inorganic matter, such as, silica glass, borosilicate glass, silicon nitride, alumina and silicon carbide may be used, and those wherein a thin film made of insulating material is coated on silicon surface with silicon dioxide, silicon nitride or tantalum oxide may also be used. Further, two or more of these may be used simultaneously.

Further, the valve 109*a* and the valve 109*b* mounted at the inlet 102 and the outlet 103 may be equipped with a control valve, such as, a check valve or a stop valve to control flow of the gaseous sample.

Then, an instrument to determine flow rate of the gaseous sample may be mounted at the inlet 102 and the outlet 103. As the instrument, an integrating flowmeter or mass flowmeter may be used. Alternatively, any suitable flow instrument may be utilized.

Further, during introduction of the gaseous sample, when pressure is applied to the inlet 102, an electric power pump, such as, a diaphragm pump, peristaltic pump or syringe pump may be used. Alternatively, the gaseous sample may be introduced manually with a syringe or dropper.

During introduction of the gaseous sample, pressure may also be drawn from the outlet 103 using an electric power pump, such as, a diaphragm pump, peristaltic pump or syringe pump Alternatively, as noted the gaseous sample may be introduced manually with a syringe or dropper.

Further, a heat dissipation fin may be mounted at a heat dissipation area in the primary refrigerator 105 and the secondary refrigerator 108. Alternatively, the heat dissipation area may be chilled with water, air, a thermoelectric element or other suitable methods. In addition, two or more of these techniques may be used simultaneously.

Although the atomizing electrode 104 preferably employs metal, any material which has good electrical conductivity or good thermal conductivity may also be utilized.

According to the embodiment of the present disclosure, one or more atomizing electrodes 104 may be used. When plural atomizing electrodes 104 are used, they may be arranged one dimensionally, such as, linearly, two dimensionally, such as, circularly, parabolic, ovally, tetragonal lattice form, rhombic lattice form, closest packing lattice form, radially, randomly, or three dimensionally like spherically, parabolic curved form or ovally curved form.

Although the capture electrode 107 preferably employs metal, any material which has good electrical conductivity or good thermal conductivity may also be utilized.

Further, according to the embodiment of the present disclosure, one or more capture electrode 107 may be used. When plural capture electrodes 107 are used, they may be arranged one dimensionally, such as, linearly, two dimensionally, such as, circularly, parabolic, ovally, tetragonal lattice form, rhombic lattice form, closest packing lattice form, radially, randomly, or three dimensionally, such as, spherically, parabolic curved form or ovally curved form.

Embodiment 2

FIGS. 5-7 are exemplary schematic views illustrating a method for collecting gaseous samples according to Embodiment 2 of the present disclosure. The same symbols were allocated to the elements in FIGS. 5-7 according to the corresponding identical elements in FIGS. 1-4 and any description of such elements has been omitted.

First, the gaseous sample 203 consisting of water 201 and chemical substance 202*a*, 202*b* is introduced into the container 101 through the inlet 102. FIG. 5 (*a*) illustrates the introduction of the gaseous sample. Gaseous sample detector may be mounted in the container 101 to confirm whether or not the container 101 is filled with the gaseous sample 203. One or more gaseous sample detectors can be mounted. According to the present disclosure, any kind and position of the gaseous sample detectors can be utilized.

During introduction of the gaseous sample, the gaseous sample 203 is preferably placed into the container 101 from the inlet 102, though the gaseous sample may be placed into the container by depressurizing the outlet 103.

Further, during introduction of the gaseous sample, prior to introducing the gaseous sample 203 into the container 101, the container 101 is preferably filled with fresh air. Container 101 may be filled with dry nitrogen gas or the other inactive gas. Alternatively, it may be filled with standard gas or calibration gas wherein the humidity is equivalent to that of the gaseous sample.

Then, during introduction of the gaseous sample, excessive gaseous sample 203 is exhausted through outlet 103.

Introduction and exhaustion of the gaseous sample 203 during introduction of the gaseous sample is controlled by the valve 109*a* and the valve 109*b*. Traps may be mounted at the inlet 102 so as not to introduce unnecessary products.

For convenience sake, FIG. 5 (*a*) does not include any substance except for chemical substances 202*a*, 202*b*, but the gaseous sample 203 may include two or more components.

Then, during production of the primary condensate, the atomizing electrode 104 is chilled by the primary refrigerator 105. FIG. 5 (*b*) illustrates production of the primary condensate. By producing the primary condensate after introduction of the gaseous sample, any condensation on the substances except for such gaseous sample can be controlled. During the producing of the primary condensate, it is preferable to decrease thermal conductivity so as not to chill any part except for the atomizing electrode 104, for example, the container 101. In order to decrease the thermal conductivity, it is preferable to reduce the contact area between the atomizing electrode 104 and the container 101. Alternatively, any material having a reduced coefficient of thermal conductivity may be disposed at the contact space between the atomizing electrode 104 and the container 101.

Then, during production of the primary condensate, the primary condensate 204 comprising water 201, the chemical substance 202*a* and the chemical substance 202*b* are formed on the outer peripheral surface of the chilled atomizing electrode 104. FIG. 5 (*c*) illustrates production of the primary condensate.

When producing of primary condensate, it is preferable to appropriately control the temperature of the atomizing electrode 104 with the primary refrigerator 105 so as not to generate an excess amount of the primary condensate 204.

According to the embodiment of the present disclosure, when the primary condensate 204 is fully produced during production of the primary condensate, the valve 109*a* and the valve 109*b* are closed. Thereafter, air can not communicate between the inner chamber of the container 101 and the outside of the container.

Then, during production of the charged microparticles, numerous charged microparticles 205 are formed from the primary condensate 204. FIG. 6 (*a*) illustrates production of the charged microparticles. Such charged microparticles are most preferably microparticles consisting of several thousand molecules, but they may be single through several hundred clusters or be several ten thousand liquid droplets. In additiona, two or more of these may be used simultaneously.

Black valves 109*a* and 109*b* in FIG. 6 (*a*) indicated that the valves are closed.

Charged microparticles 205 may also include ions or radicals from chemical substances in addition to electrically neutral molecules. They may be used simultaneously. Charged microparticles 205 are preferably charged negatively, but they may be charged positively.

During production of the charged microparticles, a voltage of from 4 kV or more to 6 kV or less is preferably applied between the atomizing electrode 104 and the opposite electrode 106.

The diameter of the charged microparticles 205 is not particularly limited according to the present disclosure, but the diameter is restricted preferably to the range of from 2 nm or more to 30 nm or less in view of stability of the charged microparticles.

An electrical amount to be charged to the charged microparticles 205 is most preferably an amount equivalent to the electrical charge content ($1.6\times10^{-19}$ C) per the single microparticle, but such amount can be changed to be larger than the electrical charge content.

Then, during application of the voltage, voltage is applied to the capture electrode 107 for the opposite electrode 106. FIG. 6 (*b*) illustrates applying of the voltage. Charged microparticles 205 having the diameter of from about 2 nm to about 30 nm tend to be dispersed because they are repulsed by static electricity, but most of the charged microparticles 205 are easily concentrated adjacent to the tip of the capture electrode 107 by providing the acicular capture electrode 107 and concentrating static electricity at the capture electrode. When the charged microparticles 205 are negatively charged, it is preferable to apply direct positive voltage to the capture electrode 107 for the opposite electrode 106. Application of the voltage is preferably continuous, but it may be applied in a pulsed manner.

Then, during production of the secondary condensate, the capture electrode 107 is chilled by the secondary refrigerator 108. FIG. 6 (*c*) illustrates the producing of the secondary condensate. By producing the secondary condensate after application of the voltage, charged microparticles 205 are concentrated adjacent to the tip of the capture electrode 107 and can be chilled.

When producing the secondary condensate, most of the charged microparticles 205 are condensed adjacent to the tip of the capture electrode 107, and the secondary condensates 206 are formed. FIG. 7 illustrates production of the secondary condensate. As a result of producing of the secondary condensate, it prevents the capture electrode 107 from spreading the secondary condensate 206 on the whole surface thereof.

In the meantime, according to the embodiment of the present disclosure, the container 101 is sealed after production of the charged microparticles. Accordingly, motion of the charged microparticles 205 would not be disturbed by air flow generated when introducing the gaseous sample 203. This is because motion of the charged microparticles 205 preferably relies mainly on static electricity. As a result, the charged microparticles 205 can easily be concentrated at the tip of the capture electrode 107.

Embodiment 3

FIGS. 8-10 are exemplary schematic views illustrating a method for collecting the gaseous sample according to Embodiment 3 of the present disclosure. The same symbols were allocated to the elements in FIGS. 8-10 according to the corresponding identical elements in FIGS. 1-4 and any description of such elements has been omitted.

First, the gaseous sample 203 consisting of water 201 and chemical substance 202*a*, 202*b* is introduced into the container 101 through the inlet 102. FIG. 8 (*a*) illustrates the introducing of the gaseous sample. Gaseous sample detector may be mounted in the container 101 to confirm whether or not the container 101 is filled with the gaseous sample 203. One or more gaseous sample detectors may be mounted and utilized. According to the present disclosure, any suitable kind and position of the gaseous sample detector can be utilized.

During introduction of the gaseous sample, the gaseous sample 203 is preferably placed into the container 101 from the inlet 102, though the gaseous sample may also be placed into the container by depressurizing the outlet 103.

Further, during introduction of the gaseous sample, prior to introducing the gaseous sample 203 into the container 101, the container 101 is preferably filled with fresh air. Container 101 may be filled with dry nitrogen gas or another inactive gas. Alternatively, it may be filled with standard gas or calibration gas where their humidity is equivalent to that of the gaseous sample.

Then, during introduction of the gaseous sample, any excessive gaseous sample 203 is exhausted through outlet 103.

Introduction and exhaustion of the gaseous sample 203 during introduction of the gaseous sample are controlled by the valve 109*a* and the valve 109*b*. Traps may be mounted at the inlet 102 so as to prevent the introduction of unnecessary products.

For convenience sake, FIG. 8 (*a*) does not include any substance except for chemical substances 202*a*, 202*b*, but the gaseous sample 203 may includes two or more components.

According to the embodiment of the present disclosure, when the gaseous sample 203 is uniformly saturated during the introducing thereof, the valve 109*a* and the valve 109*b* are then closed. Thereafter, air can not communicate between the inner chamber of the container 101 and the outside of the container 101.

Then, during the production of the primary condensate, the atomizing electrode 104 is chilled by the primary refrigerator 105. FIG. 8 (*b*) illustrates production of the primary condensate. By producing the primary condensate after introduction of the gaseous sample, any condensation on the substances except for such gaseous sample can be controlled. During production of the primary condensate, it is preferable to decrease thermal conductivity so as not to chill any part except for the atomizing electrode 104, for example, the container 101. In order to decrease the thermal conductivity, it is most preferable to reduce the contact area between the atomizing electrode 104 and the container 101. Alternatively, any material having a low coefficient of thermal conductivity may be disposed at the contact space between the atomizing electrode 104 and the container 101.

Then, during production of the primary condensate, the primary condensate 204 comprising water 201, the chemical substance 202*a* and the chemical substance 202*b* are formed on the outer peripheral surface of the chilled atomizing electrode 104. FIG. 8 (*c*) illustrates the production of the primary condensate.

During production of the primary condensate, it is preferable to control the temperature of the atomizing electrode 104 with the primary refrigerator 105 so that an excess amount of the primary condensate 204 is not generated.

Then, during production of the charged microparticles, numerous charged microparticles 205 are formed from the primary condensate 204. FIG. 9 (*a*) illustrates production of the charged microparticles. Such charged microparticles are most preferably microparticles consisting of several thousand molecules, but they may be single through several hundred clusters or be several ten thousand liquid droplets. In addition, two or more of these may be used simultaneously.

Charged microparticles 205 may also include ion or radical from chemical substances in addition to electrically neutral molecules. They may be used simultaneously. Charged microparticles 205 are preferably charged negatively, but they may be charged positively.

During production of the charged microparticles, a voltage of from 4 kV or more to 6 kV or less is preferably applied between the atomizing electrode 104 and the opposite electrode 106.

The diameter of the charged microparticles 205 is not particularly limited according to the present disclosure, but it is restricted preferably to the range of from 2 nm or more to 30 nm or less in view of stability of the charged microparticles.

An electrical amount to be charged to the charged microparticles 205 is most preferably an amount equivalent to the electrical charge content ($1.6\times10^{-19}$ C) per the single microparticle, but such an amount can be changed to be larger than the electrical charge content.

According to the embodiment of the present disclosure, the container 101 is sealed after production of the primary condensate. Thereby, the charged microparticles 205 can not flow away from the container 101.

Then, during application of the voltage, the voltage is applied to the capture electrode 107 for the opposite electrode 106. FIG. 9 (*b*) illustrates application of the voltage. Charged microparticles 205 having the diameter of from about 2 nm to about 30 nm tend to be dispersed because they are repulsed by static electricity, but most of the charged microparticles 205 are readily concentrated adjacent to the tip of the capture electrode 107 by providing the acicular capture electrode 107 and concentrating static electricity at the capture electrode 107. When the charged microparticles 205 are negatively charged, it is preferably to apply direct positive voltage to the capture electrode 107 for the opposite electrode 106. Application of the voltage is preferably continuous, but it may also be applied in a pulsed manner.

Then, during production of the secondary condensate, the capture electrode 107 is chilled by the secondary refrigerator 108. FIG. 9 (*c*) illustrates production of the secondary condensate. By producing the secondary condensate after application of the voltage, charged microparticles 205 are concentrated adjacent to the tip of the capture electrode 107 and can be chilled.

Then, during production of the secondary condensate, most of the charged microparticles 205 are condensed adjacent to the tip of the capture electrode 107, and then the secondary condensates 206 are formed. FIG. 10 illustrates the producing of the secondary condensate. As a result of producing the secondary condensate, it prevents the capture electrode 107 from spreading the secondary condensate 206 on the whole surface thereof.

Since the gaseous sample 203 is electrically neutral, it may be directly changed into condensate without producing the charged microparticles at not only the tip of the acicular capture electrode 107 but also at the side surface thereof. But, according to the embodiment of the present disclosure, since the container 101 is sealed after the primary condensate has been produced, the gaseous sample 203 would not additionally be introduced thereinto. Accordingly, it would be difficult to form condensate directly from the gaseous sample 203 on the capture electrode 107 and to spread the same on the whole surface of the capture electrode 107.

Further, according to the embodiment of the present disclosure, the charged microparticles 205 do not flow away from the container 101. At this time, since the number of the charged microparticles 205 in the container 101 would be increased, the secondary condensate 206 is concentrated at the tip of the capture electrode 107. As a result thereof, the present disclosure prevents the capture electrode 107 from spreading condensate on the whole surface thereof.

Example 1

Container 101 was made of transparent acrylic resin of 0.5 mm thickness. The container 101 was rectangular parallelepiped having dimensions of 32 mm×17 mm×12 mm. Transparent container 101 is preferable, because the process of forming condensate can be observed. In such a case, the container 101 can be made through monolithic molding.

Inlet 102 was made by forming a hole of 3 mm diameter at a part of the container 101 and connecting therewith a silicone tube of 3 mm outer diameter. Inlet 102 can be made by any method known in the art. Namely, it can be made by any method including monolithic molding to be employed to form it together with the container 101, cutting operation, and the other conventional forming methods like dry etching, hot embossing and nanoimprint.

Outlet 103 was made by forming a hole of 3 mm diameter at another part of the container 101 and connecting therewith a silicone tube of 3 mm outer diameter. Outlet 103 can be made by any method known in the art. Namely, it can be made by any method including monolithic molding to be employed to form it together with the container 101, cutting operation, and the other conventional forming methods like dry etching, hot embossing and nanoimprint.

A stainless steel needle as the atomizing electrode 104 was mounted on the inside of the container 101. The length of the stainless steel needle was 3 mm. The maximum diameter of the stainless steel needle was 0.79 mm, while the minimum diameter was 0.5 mm. The stainless steel needle had a ball having a 0.72 mm diameter at the tip thereof to stably produce charged microparticles. Further, the ball has a semispherical projection having 100 μm diameter at the tip thereof. One edge of the atomizing electrode 104 was connected to a lead for voltage application. The atomizing electrode 104 was mounted on the bottom of the container 101. The tip of the atomizing electrode 104 was mounted to extend upwardly.

A thermoelectric element as the primary refrigerator 105 was mounted adjacent to the atomizing electrode 104. The size of the thermoelectric element was 14 mm×14 mm×1 mm. The thermoelectric element had 0.9 W of maximum endotherm and 69° C. of maximum temperature difference. The surface to be chilled in the thermoelectric element was coated with ceramic. Since the surface of such ceramic has fine rough structure and porous structure, it can effectively chill any subject to be contacted therewith. Primary refrigerator 105 was connected to the atomizing electrode 104 with a thermal conductive paste.

Opposite electrode 106 was mounted by making 3 mm space from the tip of the atomizing electrode 104. As the opposite electrode 106, circular stainless plate having 12 mm outer diameter, 8 mm inner diameter and 0.47 mm thickness was utilized. One edge of the opposite electrode 106 was connected to a lead for voltage application.

A stainless steel needle as the capture electrode 107 was mounted at adjacent to the opposite electrode 106. Length of the stainless steel needle was 3 mm. Maximum diameter of the stainless steel needle was 0.79 mm, while the minimum diameter of which was 0.5 mm. Then the stainless steel needle had a ball having 0.72 mm diameter at the tip thereof. Further, the ball has semispherical projection having 100 μm diameter at the tip thereof. Tip of the capture electrode 107 was mounted to direct toward downwardly. One edge of the capture electrode 107 was connected to a lead for voltage application.

A thermoelectric element as the secondary refrigerator 108 was mounted adjacent to the capture electrode 107. The size of the thermoelectric element was 14 mm×14 mm×1 mm. The thermoelectric element had 0.9 W of maximum endotherm and 69° C. of maximum temperature difference. The surface to be chilled in the thermoelectric element was coated with ceramic. Since the surface of such ceramic has fine rough structure and porous structure, it can effectively chill any subject to be contacted therewith. Secondary refrigerator 108 was connected to the capture electrode 107 with thermal conductive paste.

Operation procedures of the electrostatic atomizer are as follows.

During introduction of the gaseous sample, the gas sample was injected into the container 101 through the inlet 102. The container 101 according to this example has 6.5 ml of volume and the gaseous sample was injected thereinto utilizing a flow rate of 500 ml/min.

According to this example, the gaseous sample was prepared by successively introducing dry nitrogen gas into water and 0.3% acetic acid solution and bubbling those.

During introduction of the gaseous sample, prior to injection of the gaseous sample into the container 101, the container 101 had been filled with dry nitrogen gas.

Then, during introduction of the gaseous sample, the excessive gaseous sample was exhausted through outlet 103.

Then, the atomizing electrode 104 was primarily chilled with a thermoelectric element. Temperature of the atomizing electrode 104 was 26° C. prior to the operation and was decreased to 15° C. 30 seconds later. The temperature of the atomizing electrode 104 was determined with a K-type thermocouple. Preferably, the temperature of the atomizing electrode 104 is maintained at the condensation point of water vapour or less.

Then, during production of the primary condensate, the primary condensate 204 was going to be formed on the outer peripheral surface of the atomizing electrode 104 at 5 seconds after commencement of operation of the thermoelectric element. Although the diameter of liquid droplets is 10 μm or less at the early stage of forming the primary condensate 204, they increase in size and sufficient amounts thereof could be taken at 10 seconds after commencement of operation of the thermoelectric element. Forming of the primary condensate 204 on the atomizing electrode 104 was observed with microscope (KEYENCE, VH-6300).

Next, in producing the charged microparticles, the primary condensates 204 were converted into numerous charged microparticles 205. Charged microparticles 205 were produced with electrostatic atomization. As stated in the foregoing Embodiment 1, although corona discharge was generated at early stage of such electrostatic atomization, the present disclosure may include it in producing the charged microparticles.

In view of stability on the charged microparticles 205, the diameter of charged microparticles 205 should preferably be adjusted within from 2 nm or more to 30 nm or less. Charged microparticles 205 exist preferably individually, but they may also consist of the combined plural microparticles.

During production of the charged microparticles, 5 kV direct current (DC) was applied between the atomizing electrode 104 and the opposite electrode 106. In this case, the atomizing electrode 104 was used as a cathode, while the opposite electrode 106 was used as an anode. Although a similar effect was confirmed when the atomizing electrode 104 was used as an anode and the opposite electrode 106 was used as a cathode, the process for producing the charged microparticles was relatively unstable.

During production of charged microparticles, a conical water column, referred to as a Taylor cone, was formed at the tip of the atomizing electrode 104 and numerous charged microparticles containing chemical substances were released from the tip of the water column. FIG. 11 is the schematic view illustrating a Taylor cone and a method for producing the charged microparticles. Primary condensates 302, which form the Taylor cone 301, were successively transferred toward the tip of the atomizing electrode 104. Charged microparticles 303 were formed from tip of the tail cone 301 where the electrical field is concentrated.

Then, during production of the charged microparticles, electric current flowed across between the atomizing electrode 104 and the opposite electrode 106 was determined. When excessive electric current flowed therebetween, the voltage to be applied between the atomizing electrode 104 and the opposite electrode 106 was eliminated or reduced.

Further, during application of the voltage, 500V of direct current (DC) was applied between the opposite electrode 106 and the capture electrode 107. By applying such voltage, charged microparticles 205 can be captured adjacent to the tip of the capture electrode 107 with static electricity. According to this EXAMPLE, positive voltage was applied to the capture electrode 107 for the opposite electrode 106. Voltage to be applied between the opposite electrode 106 and the capture electrode 107 should preferably be adjusted to from 0 V or more to 5 kV or less, more preferably from 0 V or more to 500V or less. When the charged microparticles 205 are negatively charged, it is most preferable to apply a positive voltage to the capture electrode 107.

Then, the capture electrode 107 was secondary chilled with the secondary refrigerator 108. Temperature of the capture electrode 107 was 26° C. prior to this operation and was decreased to 15° C. 30 seconds later. Temperature of the capture electrode 107 was determined with a K-type thermocouple. Preferably, the temperature of the capture electrode 107 is maintained at the condensation point of water vapour or less. By applying voltage to the capture electrode 107 and secondary chilling the same, substantially all of the charged microparticles 205 can be chilled adjacent to the tip of the capture electrode 107.

During production of the secondary condensate, secondary condensate 206 had been taken by condensing the charged microparticles 205 adjacent to the capture electrode 107. Preferably, the temperature of the capture electrode 107 should be changed appropriately according to an amount of the secondary condensate 206 produced. In view of the life expectancy of the charged microparticles 205, production of the secondary condensate should be initiated within at least 10 minutes from commencement of production of the charged microparticles.

FIG. 12(*a*) is an exemplary schematic view illustrating the capture electrode 107 at the step of preparing secondary condensate, while FIG. 12(*b*) is a photograph of the tip of the electrode taken by a light microscope. Obviously from FIGS. 12(*a*) and 12(*b*), the secondary condensate 401 can be captured adjacent to the tip of the capture electrode 107. Spread of liquid droplet had been prevented, because the secondary condensate 401 charged static electricity. Further, since the tip of the capture electrode 107 was directed downwardly, spread of liquid droplet had also been prevented due to gravity applied to the secondary condensate 401.

After producing the secondary condensate, about 1 μl of secondary condensate 206 was accumulated adjacent to the tip of the capture electrode 107. Two minutes was necessary from the introduction of the gaseous sample to the production of the secondary condensate.

In order to confirm the presence of acetic acid in the secondary condensate 206, the secondary condensate 206 was removed with a syringe and was subjected to gas chromatograph assay. The assay was performed with GC-4000 from G.L. Science.

FIG. 13 illustrates the assay result on the secondary condensate 206. The vertical axis corresponds to the peak area of gas chromatogram on acetic acid wherein the larger peak area indicates the higher acetic acid concentration in the secondary condensate 206. The horizontal axis corresponds to voltage $V_c$ to be applied to capture electrode 107 for the opposite electrode 106. Capture voltage $V_c$ should be denoted as plus, when the opposite electrode is the cathode and the capture electrode is the anode.

In is clear from FIG. 13 that the secondary condensate 206 contained acetic acid. Acetic acid concentration in the secondary condensate 206 tended to be increased according to the larger capture voltage $V_c$, in particular, acetic acid concentration in the secondary condensate 206 was approximately double in comparison $V_c$=500V with $V_c$=0V. This indicated that the present disclosure offered the secondary effect of concentrating electrostatically atomized solution.

The result of FIG. 13 indicated that it is effective to secondary chill the capture electrode 107 after voltage is applied to the same. Result of $V_c$=500V was obtained by applying voltage to the capture electrode 107 and secondary chilling the same. Result of $V_c$=0V was obtained by secondary chilling the capture electrode 107 and applying voltage to the same. The concentration of the secondary condensate 206 produced by applying voltage to the capture electrode 107 and secondary chilling the same was higher than that produced by secondary chilling the capture electrode 107 and applying voltage to the same. It is therefore preferable to secondary chill the capture electrode 107 after voltage is applied to the same.

Assay conditions were as follows. Capillary column was employed as assay column. Capillary column has an inner diameter of 0.53 mm and a length of 30 m. Helium was used as the carrier gas. Temperature of an oven was set for 160° C. Temperature of injection and of hydrogen flame ionization detector (FID) were respectively set for 250° C.

After completing the assay, the capture electrode 107 was detached from the container 101 and was rinsed with methanol.

Then the capture electrode 107 was heated to remove the secondary condensate 206 on the capture electrode 107. Thermoelectric element was used to heat the capture electrode 107. The thermoelectric element used in this step is the same type of element utilized to chill the capture electrode 107 to produce the secondary condensate. Voltage polarity to be applied to the thermoelectric element to heat the capture electrode 107 is reverse to that necessary to chill the capture electrode 107.

Further, in the production of charged microparticles and application of voltage, the capture electrode 107 was destaticized. Such destaticization was performed by grounding the capture electrode 107.

Then, from the introduction of the gaseous sample to the production of the secondary condensate, the temperature of the opposite electrode 106 was maintained at the condensation point of water vapour or higher. Thereby, no condensate appeared on outer peripheral surface of the opposite electrode 106.

Example 2

Description of system employed herein is intentionally omitted, because the system is identical to that of Example 1. Accordingly, only operation procedures of the electrostatic atomizer will be described below.

During introduction of the gaseous sample, it was injected into the container 101 through the inlet 102. The container 101 according to this example has 6.5 ml of volume and the gaseous sample was injected thereinto with a flow rate of 500 ml/min.

According to this example, the gaseous sample was prepared by successively introducing dry nitrogen gas into water and 0.3% acetic acid solution and bubbling those.

During introduction of the gaseous sample, prior to injection of the gaseous sample into the container 101, the container 101 had been filled with dry nitrogen gas.

Then, during introduction of the gaseous sample, the excessive gaseous sample had been exhausted through outlet 103.

Then, the atomizing electrode 104 was primarily chilled with a thermoelectric element. Temperature of the atomizing electrode 104 was 26° C. prior to the operation and was decreased to 15° C. 30 seconds later. Temperature of the atomizing electrode 104 was determined with a K-type thermocouple. Preferably, the temperature of the atomizing electrode 104 is maintained at the condensation point of water vapour or less.

Then, during production of the primary condensate, the primary condensate 204 was going to be formed on the outer peripheral surface of the atomizing electrode 104 at 5 seconds later from commencement on operation of the thermoelectric element. Although the diameter of liquid droplets is 10 μm or less at the early stage of forming the primary condensate 204, they increase and sufficient amounts thereof could be taken at 10 seconds after commencement of operation of the thermoelectric element. Forming of the primary condensate 204 on the atomizing electrode 104 was observed with microscope (KEYENCE, VH-6300).

Prior to producing the charged microparticles, the valves 109*a* and 109*b* equipped with the inlet 102 and the outlet 103 respectively were closed. Thereby, introduction of the gaseous sample 203 into the container 101 was terminated.

Next, in the production of the charged microparticles, the primary condensates 204 were converted into numerous charged microparticles 205. Charged microparticles 205 were produced with electrostatic atomization. As stated in the foregoing Embodiment 1, although corona discharge was generated at the early stage of such electrostatic atomization, the present disclosure may include it in producing of the charged microparticles.

In view of stability on the charged microparticles 205, diameter of charged microparticles 205 should preferably be adjusted within from 2 nm or more to 30 nm or less. Charged microparticles 205 exist preferably individually, but they may also consist of the combined plural microparticles.

Then, during production of charged microparticles, 5 kV direct current (DC) was applied between the atomizing electrode 104 and the opposite electrode 106. In this case, the atomizing electrode 104 was used as a cathode, while the opposite electrode 106 was used as an anode.

During production of charged microparticles, a conical water column, referred to as a Taylor cone, was formed at the tip of the atomizing electrode 104 and numerous charged microparticles containing chemical substances were released from the tip of the water column.

Then, during production of charged microparticles, it was determined that electric current flowed across between the atomizing electrode 104 and the opposite electrode 106. When excessive electric current flowed therebetween, voltage to be applied to between the atomizing electrode 104 and the opposite electrode 106 was eliminated or reduced.

Further, during application of the voltage, 500V of direct current (DC) was applied between the opposite electrode 106 and the capture electrode 107. By applying such a voltage, charged microparticles 205 can be captured adjacent to the tip of the capture electrode 107 with static electricity. According to this EXAMPLE, positive voltage was applied to the capture electrode 107 for the opposite electrode 106. Voltage to be applied between the opposite electrode 106 and the capture electrode 107 should preferably be adjusted within the range from 0 V or more to 5 kV or less, more preferably from 0 V or more to 500V or less. When the charged microparticles 205 are negatively charged, it is most preferable to apply positive voltage to the capture electrode 107.

Then, the capture electrode 107 was secondary chilled with the secondary refrigerator 108. Temperature of the capture electrode 107 was 26° C. prior to the operation and was decreased to 15° C. 30 seconds later. Temperature of the capture electrode 107 was determined with a K-type thermocouple. Preferably, temperature of the capture electrode 107 is maintained at the condensation point of water vapour or less.

During production of the secondary condensate, secondary condensate 206 had been taken by condensing the charged microparticles 205 adjacent to the capture electrode 107. Preferably, temperature of the capture electrode 107 should be changed appropriately according to an amount of the secondary condensate 206 produced. In view of life expectancy of the charged microparticles 205, production of the secondary condensate should be initiated within at least 10 minutes from commencement of production of the charged microparticles.

By producing the foregoing secondary condensate, approximately 1 μl of the secondary condensate could be accumulated adjacent to the tip of the capture electrode 107.

Example 3

Description of the system employed herein is intentionally omitted, because the system is identical to that of Example 1. Accordingly, only operation procedures of the electrostatic atomizer will be described below.

During introduction of the gaseous sample, the gaseous sample was injected into the container 101 through the inlet 102. The container 101 according to this example has 6.5 ml of volume and the gaseous sample was injected thereinto with a flow rate of 500 ml/min.

According to this example, the gaseous sample was prepared by successively introducing dry nitrogen gas into water and 0.3% acetic acid solution and bubbling those.

During introduction of the gaseous sample, prior to injection of the gaseous sample into the container 101, the container 101 had been filled with dry nitrogen gas.

Then, during introduction of the gaseous sample, the excessive gaseous sample had been exhausted through outlet 103.

Prior to the primary chill, the valves 109*a* and 109*b* equipped with the inlet 102 and the outlet 103 respectively were closed. Thereby, introduction of the gaseous sample 203 into the container 101 was terminated.

Then, the atomizing electrode 104 was primarily chilled with a thermoelectric element. Temperature of the atomizing electrode 104 was 26° C. prior to the operation and was decreased to 15° C. 30 seconds later. Temperature of the atomizing electrode 104 was determined with a K-type thermocouple. Preferably, temperature of the atomizing electrode 104 is maintained at the condensation point of water vapour or less.

Then, during production of the primary condensate, the primary condensate 204 was going to be formed on the outer peripheral surface of the atomizing electrode 104 5 seconds after commencement of operation of the thermoelectric element. Although the diameter of liquid droplets is 10 μm or less at the early stage of forming the primary condensate 204, they increase and sufficient amounts thereof could be taken at 10 seconds after commencement of operation of the thermoelectric element. Forming of the primary condensate 204 on the atomizing electrode 104 was observed with microscope (KEYENCE, VH-6300).

Next, in the producing of the charged microparticles, the primary condensates 204 were converted into numerous charged microparticles 205. Charged microparticles 205 were produced with electrostatic atomization. As stated in the foregoing Embodiment 1, although corona discharge was generated at early stage of such electrostatic atomization, the present disclosure may include it in producing of the charged microparticles.

In view of stability of the charged microparticles 205, the diameter of charged microparticles 205 should preferably be adjusted within the range from 2 nm or more to 30 nm or less. Charged microparticles 205 exist preferably individually, but they may also consist of the combined plural microparticles.

Then, during production of charged microparticles, 5 kV direct current (DC) was applied between the atomizing electrode 104 and the opposite electrode 106. In this case, the atomizing electrode 104 was used as a cathode, while the opposite electrode 106 was used as an anode.

During production of charged microparticles, a conical water column, referred to as a Taylor cone, was formed at the tip of the atomizing electrode 104 and numerous charged microparticles containing chemical substances were released from the tip of the water column.

Then, during production of charged microparticles, it was determined that electric current flowed across between the atomizing electrode 104 and the opposite electrode 106. When excessive electric current flowed therebetween, the voltage to be applied to between the atomizing electrode 104 and the opposite electrode 106 was eliminated or reduced.

Further, during application of the voltage, 500V of direct current (DC) was applied to between the opposite electrode 106 and the capture electrode 107. By applying such a voltage, charged microparticles 205 can be captured adjacent to the tip of the capture electrode 107 with static electricity. According to this EXAMPLE, positive voltage was applied to the capture electrode 107 for the opposite electrode 106. Voltage to be applied between the opposite electrode 106 and the capture electrode 107 should preferably be adjusted to from 0 V or more to 5 kV or less, more preferably from 0 V or more to 500V or less. When the charged microparticles 205 are negatively charged, it is most preferable to apply a positive voltage to the capture electrode 107.

Then, the capture electrode 107 was secondary chilled with the secondary refrigerator 108. Temperature of the capture electrode 107 was 26° C. prior to the operation and was decreased to 15° C. 30 seconds later. Temperature of the capture electrode 107 was determined with a K-type thermocouple. Preferably, temperature of the capture electrode 107 is maintained at the condensation point of water vapour or less.

During production of the secondary condensate, secondary condensate 206 had been taken by condensing the charged microparticles 205 adjacent to the capture electrode 107. Preferably, temperature of the capture electrode 107 should be changed appropriately according to an amount of the secondary condensate 206 produced. In view of life expectancy of the charged microparticles 205, production of the secondary condensate should be initiated within at least 10 minutes from commencement of production of the charged microparticles.

By producing the foregoing secondary condensate, approximately 1 μm of the secondary condensate could be accumulated adjacent to the tip of the capture electrode 107.

It is obvious to one skilled in the art to predict many modifications and variations upon consideration of the disclosure herein. The foregoing disclosure should therefore be interpreted as an illustration. Modifications regarding the details of disclosed embodiments may be made without departing from the spirit of the present disclosure.

INDUSTRIAL APPLICABILITY

Since a method for collecting gaseous sample according to the present disclosure can prevent the capture electrode from spreading solution electrostatically atomized thereon, it would be effective to use wherein trace components in the gaseous sample have to be assayed. The method can be applied to a field of environment, chemical engineering, food processing and medicine in the form of, for example, but not limited to, a monitor for air pollution or water pollution and a biomarker assay device.

We claim:

1. A method for collecting a gaseous sample with an electrostatic atomizer, comprising:

preparing the electrostatic atomizer comprising a sealable container, an inlet for the gaseous sample mounted at a part of the container, an outlet for the gaseous sample mounted at another part of the container, an atomizing electrode mounted in the container, a primary refrigerator to chill the atomizing electrode, an opposite electrode mounted in the container and having a slit, an acicular capture electrode opposed to the opposite electrode through the slit positioned therebetween, and a secondary refrigerator to chill the capture electrode, introducing the gaseous sample into the container through the inlet, chilling the atomizing electrode with the primary refrigerator, preparing a primary condensate from the gaseous sample on an outer peripheral surface of the atomizing electrode, preparing charged microparticles from the primary condensate with electrostatic atomization, applying voltage to the capture electrode for the opposite electrode, chilling the capture electrode with the secondary refrigerator, and preparing a secondary condensate from the charged microparticles at a position adjacent to the tip of the capture electrode.

2. The method according to claim 1 wherein the introduction of said gaseous sample is completed on or before initiation of preparing charged microparticles.

3. The method according to claim 1 wherein the tip of said capture electrode is directed downwardly.

4. The method according to claim 1 wherein said capture electrode is chilled with said secondary refrigerator to a condensation point of water vapor or less.

5. The method according to claim 1 wherein said secondary refrigerator is a thermoelectric element.

6. The method according to claim 5 wherein a chilling surface of said secondary refrigerator is changed to a heating surface by reversing the polarity of direct voltage to be applied to said thermoelectric element.

7. The method according to claim 1 wherein said secondary condensate is evaporated by heating said capture electrode.

8. The method according to claim 1 wherein the temperature of said opposite electrode is kept at a condensation point of water vapor or more.

9. The method according to claim 1 wherein said charged microparticles comprises water and components of said gaseous sample.

10. The method according to claim 1 wherein components of said gaseous sample are volatile organic compounds.

11. The method according to claim 10 wherein molecular weight of said volatile organic compounds is not less than 15 g/mol and not more than 500 g/mol.

12. The method according to claim 1 wherein said capture electrode possesses a destaticization system.

13. The method according to claim 1 wherein said capture electrode is able to connect to ground.

14. The method according to claim 1 wherein the tip of said capture electrode has a reservoir to receive said secondary condensate.

15. The method according to claim 1 wherein the tip of said capture electrode is equipped with a detector for chemical substances.

* * * * *